(12) United States Patent
Hayashi et al.

(10) Patent No.: US 7,887,527 B2
(45) Date of Patent: Feb. 15, 2011

(54) ABSORBENT ARTICLE AND INNER ABSORBENT ARTICLE

(75) Inventors: Akifumi Hayashi, Sakura (JP); Yoshinori Katayama, Sakura (JP); Tomoaki Ishida, Sakura (JP)

(73) Assignee: Daio Paper Corporation, Ehime (JP)

( * ) Notice: Subject to any disclaimer, the term of this patent is extended or adjusted under 35 U.S.C. 154(b) by 403 days.

(21) Appl. No.: 10/586,698

(22) PCT Filed: Jan. 21, 2005

(86) PCT No.: PCT/JP2005/000780

§ 371 (c)(1), (2), (4) Date: Jul. 20, 2006

(87) PCT Pub. No.: WO2005/070362

PCT Pub. Date: Aug. 4, 2005

(65) Prior Publication Data

US 2007/0191807 A1    Aug. 16, 2007

(30) Foreign Application Priority Data

Jan. 23, 2004  (JP) ............................. 2004-016282
Jan. 23, 2004  (JP) ............................. 2004-016314
Jan. 27, 2004  (JP) ............................. 2004-018497
Sep. 21, 2004  (JP) ............................. 2004-273917

(51) Int. Cl.
*A61F 13/15* (2006.01)
*A61F 13/20* (2006.01)

(52) U.S. Cl. ............................. 604/385.28; 604/385.04; 604/385.26

(58) Field of Classification Search ...... 604/385.24–28, 604/385.04, 385.28
See application file for complete search history.

(56) References Cited

U.S. PATENT DOCUMENTS

| 5,674,215 A | 10/1997 | Ronnberg |
| 6,287,286 B1 | 9/2001 | Akin et al. |
| 6,429,351 B1 | 8/2002 | Guidotti et al. |
| 2003/0099821 A1* | 5/2003 | Takai et al. ............... 428/292.1 |

FOREIGN PATENT DOCUMENTS

JP    62-85001 A    4/1987

(Continued)

OTHER PUBLICATIONS

English translation of the specification of JP 2000-300606 to Abiko.*

(Continued)

*Primary Examiner*—Melanie J Hand
(74) *Attorney, Agent, or Firm*—Holtz, Holtz, Goodman & Chick, PC

(57) ABSTRACT

In an absorbent article 1 including a liquid-permeable topsheet 2 positioned at a surface that contacts with a human body; a non liquid-permeable backsheet 3 positioned at a surface opposite to the topsheet 2; and an absorbent body 4 provided between the topsheet 2 and the backsheet 3, a three-dimensional gather 6 is formed by a folding portion 32 at which the backsheet 3 is folded up to the topsheet 2 side along both side portions in a longitudinal direction of the absorbent body 4, and a nonwoven fabric at least partially adhered to this folding portion 32. The three-dimensional gather 6 has a free end 62 structured with the nonwoven fabric.

4 Claims, 24 Drawing Sheets

FOREIGN PATENT DOCUMENTS

| | | |
|---|---|---|
| JP | 62-97629 U | 6/1987 |
| JP | 63-159501 A | 7/1988 |
| JP | 63-230164 A | 9/1988 |
| JP | 2-79919 U | 6/1990 |
| JP | 3-15510 U | 2/1991 |
| JP | 05-192367 | 8/1993 |
| JP | 6-57333 U | 8/1994 |
| JP | 7-000446 A | 1/1995 |
| JP | 7-21020 U | 4/1995 |
| JP | 8-503392 T | 4/1996 |
| JP | 8-182702 A | 7/1996 |
| JP | 9-056746 A | 3/1997 |
| JP | 10-052457 A | 2/1998 |
| JP | 10-137284 A | 5/1998 |
| JP | 11-104174 A | 4/1999 |
| JP | 11-197180 A | 7/1999 |
| JP | 2000-107224 A | 4/2000 |
| JP | 2000-300606 A | 10/2000 |
| JP | 2000-514672 T | 11/2000 |
| JP | 2000-333990 A | 12/2000 |
| JP | 2002-119536 A | 4/2002 |
| JP | 2002-159529 A | 6/2002 |
| JP | 2002-523140 T | 7/2002 |
| JP | 2003-506150 A | 2/2003 |
| JP | 2003-093438 A | 4/2003 |
| JP | 2003-265521 A | 9/2003 |
| WO | WO 0110372 A1 * | 2/2001 |

OTHER PUBLICATIONS

Notification Concerning Transmittal of International Preliminary Report on Patentability, Chapter I of the Patent Cooperation Treaty, and Written Opinion of the International Searching Authority for PCT/JP2005/000780, 8 sheets.

Japanese Office Action dated Feb. 9, 2010 and English translation thereof issued in a counterpart Japanese Application No. 2004-018497.

Japanese Office Action dated May 19, 2009 and English translation thereof issued in a counterpart Japanese Application No. 2004-016282.

Japanese Office Action dated Jun. 2, 2009 and English translation thereof issued in a counterpart Japanese Application No. 2004-018497.

Japanese Office Action dated May 18, 2010 and English translation thereof, issued in counterpart Japanese Application No. 2004-018497.

Japanese Office Action dated May 25, 2010 and English translation thereof, issued in counterpart Japanese Application No. 2006-007773.

Japanese Office Action dated May 19, 2009 and English translation thereof issued in a counterpart Japanese Application No. 2004-016282.

Japanese Office Action dated Jun. 2, 2009 and English translation thereof issued in a counterpart Japanese Application No. 2004-018497.

Japanese Office Action dated Oct. 19, 2010 (and English translation thereof) in counterpart Japanese Application No. 2006-007773.

* cited by examiner

ABSORBENT ARTICLE AND INNER ABSORBENT ARTICLE

This application is a U.S. National Phase Application under 35 USC 371 of International Application PCT/JP2005/000780 filed Jan. 21, 2005.

FIELD OF THE INVENTION

The present invention relates to an absorbent article and an inner absorbent article.

DESCRIPTION OF THE BACKGROUND

Conventionally, among absorbent pads provided as diapers by being adhered to diapers or external member of diapers for example, the one including a three-dimensional gather for the purpose of preventing body fluid absorbed by an absorbent body from being leaked or oozed out has been known. Among methods for providing a three-dimensional gather, a known method for example is to provide a three-dimensional gather by adhering, to a top surface of a topsheet, a separate nonwoven fabric (nonwoven fabric applied with water repellant treatment or waterproof treatment) through which liquid is difficult to permeate as a gather sheet (see Patent Document 1 for example). Patent Document 1: Japanese Laid-open Patent Specification No. 2003-265521

DISCLOSURE OF THE INVENTION

Problem to be Solved by the Invention

In the case of the absorbent pad disclosed in Patent Document 1 however, the three-dimensional gather is formed by adhering, to an upper face of the topsheet, another nonwoven fabric through which liquid is difficult to permeate (nonwoven fabric applied with water repellant treatment or waterproof treatment) for example. Thus, even when the three-dimensional gather contacts with a human body, the human body does not have a pricking feeling and thus does not impair the sense of use. However, leakage or oozing of body fluid from the upper face of the topsheet was not prevented completely. This has caused a problem where a user feels insecurity or feels discomfort due to the leakage or oozing.

It is an object of the present invention to provide an absorbent article and an inner absorbent article having a three-dimensional gather that can prevent body fluid from being leaked or oozed out.

Means for Solving the Problem

In order to solve the above problem, the present invention according to a first aspect is an absorbent article comprising: a liquid-permeable topsheet positioned at a surface that contacts with a human body; a non liquid-permeable backsheet positioned at a surface opposite to the topsheet; and an absorbent body provided between the topsheet and the backsheet; wherein: a three-dimensional gather is formed by a folding portion at which the backsheet is folded up to the topsheet side substantially along both side portions in a longitudinal direction of the absorbent body and a nonwoven fabric at least partially adhered to the folding portion; and the three-dimensional gather has a free end structured with the nonwoven fabric.

The present invention according to another aspect is the absorbent article wherein the nonwoven fabric is adhered to a surface opposite to a surface of the folding portion that faces the topsheet.

The present invention according to another aspect is the absorbent article wherein the nonwoven fabric is adhered to the backsheet from an adhesion starting point at an inner side in a width direction than a folding starting point of the folding portion.

The present invention according to another aspect is the absorbent article wherein the nonwoven fabric is adhered to a surface of the folding portion that faces the topsheet.

The present invention according to another aspect is the absorbent article wherein the nonwoven fabric is adhered to the topsheet.

The present invention according to another aspect is an absorbent article comprising: a liquid-permeable topsheet positioned at a surface that contacts with a human body; a non liquid-permeable backsheet positioned at a surface opposite to the topsheet; and an absorbent body provided between the topsheet and the backsheet; wherein: a three-dimensional gather is formed by covering both surfaces of a folding portion of the backsheet folded up to the topsheet side substantially along both side portions in a longitudinal direction of the absorbent body, by extending the topsheet.

The present invention according to another aspect is the absorbent article wherein a region of the topsheet positioned at an upper face of the absorbent body is liquid-permeable, while a region that covers the backsheet is less liquid-permeable than the region positioned at the upper face of the absorbent body.

The present invention according to another aspect is an absorbent article comprising: a liquid-permeable topsheet positioned at a surface that contacts with a human body; a non liquid-permeable backsheet positioned at a surface opposite to the topsheet; an absorbent body provided between the topsheet and the backsheet; and a three-dimensional gather formed at the topsheet side to be raised at both side portions in a longitudinal direction of the absorbent body; wherein the absorbent article includes: a folding portion at which the backsheet is folded up to the topsheet side substantially along both side portions in the longitudinal direction of the absorbent body; an attachment portion at which a part of the folding portion is adhered to both side portions in the longitudinal direction of the topsheet; and an adhesion section at which the attachment portion is folded up to the topsheet side and is adhered to the topsheet; wherein the folding portion constitutes at least a part of the three-dimensional gather.

The present invention according to another aspect is the absorbent article wherein the three-dimensional gather is composed of the folding portion and a non liquid-permeable nonwoven fabric at least partially adhered to the folding portion, and the three-dimensional gather has a free end structured with the non liquid-permeable nonwoven fabric.

The present invention according to another aspect is the absorbent article wherein the non liquid-permeable nonwoven fabric is adhered to a surface opposite to a surface of the folding portion that faces the topsheet.

The present invention according to another aspect is the absorbent article wherein the non liquid-permeable nonwoven fabric is adhered to the backsheet from an adhesion starting point at an inner side in a width direction than a folding starting point of the folding portion.

The present invention according to another aspect is the absorbent article wherein: the backsheet includes a ramie nonwoven fabric; and the non liquid-permeable nonwoven fabric is adhered to a surface of the folding portion that faces the topsheet.

The present invention according to another aspect is an absorbent article comprising: a liquid-permeable topsheet positioned at a surface that contacts with a human body; a non liquid-permeable backsheet positioned at a surface opposite to the topsheet; an absorbent body provided between the topsheet and the backsheet; and a three-dimensional gather formed at the topsheet side to be raised at both side portions in a longitudinal direction of the absorbent body, wherein: the three-dimensional gather is formed by covering both surfaces of a folding portion of the backsheet folded up to the topsheet side substantially along both side portions in the longitudinal direction of the absorbent body, by extending the topsheet; and an adhesion portion is formed in a vicinity of a folding starting point of the folding portion substantially along both side portions in the longitudinal direction of the absorbent body, by folding up the topsheet to the topsheet side and adhering the topsheets to each other.

The present invention according to another aspect is the absorbent article wherein a region of the topsheet positioned at an upper face of the absorbent body is liquid-permeable, while a region that covers the backsheet is non liquid-permeable.

The present invention according to another aspect is an inner absorbent article comprising: a liquid-permeable topsheet positioned at a surface that contacts with a human body; a non liquid-permeable backsheet positioned at a surface opposite to the topsheet; and an absorbent body provided between the topsheet and the backsheet, wherein: a three-dimensional gather is formed by a folding portion at which the backsheet is folded up to the topsheet side substantially along both side portions in a longitudinal direction of the absorbent body, and a nonwoven fabric that is adhered to a surface opposite to a surface of the folding portion that faces the topsheet and is also adhered to the backsheet from an inner side in a width direction of a folding starting point of the folding portion as an adhesion starting point; and the three-dimensional gather has a free end structured with the nonwoven fabric.

The term "inner absorbent article" used herein means an absorbent article that is used by being attached to an outer such as an external member of a diaper.

The present invention according to another aspect is an inner absorbent article comprising: a liquid-permeable topsheet positioned at a surface that contacts with a human body; a non liquid-permeable backsheet positioned at a surface opposite to the topsheet; and an absorbent body provided between the topsheet and the backsheet, wherein: a three-dimensional gather is formed by a folding portion at which the backsheet is folded up to the topsheet side substantially along both side portions in a longitudinal direction of the absorbent body and a nonwoven fabric in which one end portion in the longitudinal direction is adhered to a surface of the folding portion that faces the topsheet and the other end portion in the longitudinal direction is adhered to the topsheet; and the three-dimensional gather has a free end structured with the nonwoven fabric.

The present invention according to another aspect is the absorbent article wherein the nonwoven fabric is folded up and the three-dimensional gather has a free end as a folding starting point of the nonwoven fabric.

The present invention according to another aspect is an inner absorbent article comprising: a liquid-permeable topsheet positioned at a surface that contacts with a human body; a non liquid-permeable backsheet positioned at a surface opposite to the topsheet; and an absorbent body provided between the topsheet and the backsheet, wherein: a three-dimensional gather is provided by covering both surfaces of a folding portion of the backsheet folded up to the topsheet side substantially along both side portions in a longitudinal direction of the absorbent body, by extending the topsheet.

The present invention according to another aspect is the inner absorbent article wherein the folding portion of the backsheet has a positioning mark in the longitudinal direction.

The present invention according to another aspect is the inner absorbent article wherein an interspace is provided between the topsheet and the backsheet along the longitudinal direction of both side portions in the longitudinal direction of the absorbent body.

The present invention according to another aspect is an inner absorbent article, comprising: a liquid-permeable topsheet positioned at a surface that contacts with a human body; a non liquid-permeable backsheet positioned at a surface opposite to the topsheet; an absorbent body provided between the topsheet and the backsheet; and a three-dimensional gather formed at the topsheet side to be raised at both side portions in a longitudinal direction of the absorbent body, wherein the inner absorbent article includes: a folding portion at which the backsheet is folded up to the topsheet side substantially along both side portions in the longitudinal direction of the absorbent body; an attachment portion at which a part of the folding portion is adhered to both side portions in the longitudinal direction of the topsheet; and an adhesion section at which the attachment portion is folded up to the topsheet side and is adhered to the topsheet, wherein the folding portion constitutes at least a part of the three-dimensional gather.

The present invention according to another aspect is an inner absorbent article, comprising: a liquid-permeable topsheet positioned at a surface that contacts with a human body; a non liquid-permeable backsheet positioned at a surface opposite to the topsheet; an absorbent body provided between the topsheet and the backsheet; and a three-dimensional gather formed at the topsheet side to be raised at both side portions in a longitudinal direction of the absorbent body, wherein: the three-dimensional gather is formed by covering both surfaces of a folding portion of the backsheet folded up to the topsheet side substantially along both side portions in the longitudinal direction of the absorbent body, by extending the topsheet; an adhesion portion is formed in a vicinity of a folding starting point of the folding portion substantially along both side portions in the longitudinal direction of the absorbent body, by folding up the topsheet to the topsheet side and adhering the topsheets to each other.

According to another aspect of the present invention, the backsheet is folded up to the topsheet. Thus, the backsheet covers the absorbent body so as to cover from the bottom face of the absorbent body to the side faces and a part of the upper face. This not only enables to compose the root portion of the three-dimensional gather by the backsheet made of a non liquid-permeable sheet in a three-dimensional manner, but also enables to provide the three-dimensional gather with a free end made of a nonwoven fabric.

Therefore, pricking feeling during the use can be prevented, superior sense of use can be provided, and skin troubles can be prevented.

Furthermore, when the absorbent article receives a pressure from a user body, body fluid pressed out of the absorbent body can be prevented from being leaked or oozed from the root portion of the three-dimensional gather. Furthermore, since the three-dimensional gather is composed of two layers of the backsheet and the nonwoven fabric, the leakage or oozing of body fluid can be prevented with higher security.

Furthermore, the rising edge at the root portion of the three-dimensional gather is continuously structured by the folded backsheet. This eliminates a need for providing, for example, an adhesion region to form a rising edge in the upper face of the absorbent body.

As a result, a sufficient area can be secured on the upper face of the absorbent body. Thus, when body fluid spills on the upper face of the absorbent body, the body fluid can be absorbed smoothly, thus preventing the body fluid from being leaked.

In addition, the absorbent body is wrapped in a manner as follows. A member to be wrapped is placed on an upper face of a wrapping member to cover a bottom face and side faces of the member so as to be wrapped by the wrapping member. Then, both side sections of the wrapping member that protrude from the upper face of the member to be wrapped are folded up and are fixed to, or are made free from, the member to be wrapped. This method will be hereinafter referred to as the framing method. This method eliminates a need to structure a side flap. Thus, the absorbent article is prevented from shrinking in the longitudinal direction. Thus, the absorbent article can be worn by a user smoothly.

According to another aspect of the present invention a skin contact surface of the folding portion of the folded backsheet that is a surface opposite to a face opposed to topsheet is adhered with a nonwoven fabric, thus preventing the folding portion from having a contact with a human body.

This can suppress stimulation to skin when the absorbent pad is worn by a user. This not only can improve the usability but also can reduce skin troubles.

According to another aspect of the present invention, since a nonwoven fabric is adhered to the backsheet from an inner side in the width direction of the folding starting point of the folding portion as an adhesion starting point, side faces of the absorbent body can also be covered by the nonwoven fabric. This not only improves the sense of use more securely, but also reduces skin troubles.

According to another aspect of the present invention, the backsheet is provided with clothlikeness. Thus, even when the backsheet is used as a skin contact surface, a soft sense of use can be provided to a user.

According to another aspect of the present invention, since a nonwoven fabric is adhered to both of the backsheet and the topsheet, the nonwoven fabric can be more securely fixed to the absorbent article and the three-dimensional gather is reinforced, thus effectiveness in leakage prevention is high.

Furthermore, since the three-dimensional gather composed of at least two layers of the backsheet and the nonwoven fabric, the leakage or oozing of body fluid can be more securely prevented.

According to another aspect of the present invention, the three-dimensional gather is composed of the backsheet and the topsheet that covers both surfaces of the folding portion of the backsheet.

This can prevent, when the absorbent article receives a pressure from a user body, body fluid pressed out of the absorbent body from oozing from the root of the three-dimensional gather to outside.

Furthermore, since the folding portion of the backsheet is covered by the topsheet, the folding portion is prevented from having a contact with a human body.

This suppresses stimulation to skin of a user when worn by the user. This not only improves the sense of use, but also reduces skin troubles.

Furthermore, the three-dimensional gather can have clothlikeness, thus providing a soft sense of use to a user.

According to another aspect of the present invention, since the three-dimensional gather is composed of the non liquid-permeable backsheet and a region of the topsheet that is less liquid-permeable than a region positioned at the upper face of the absorbent body, the oozing of body fluid can be more securely prevented.

Furthermore, the three-dimensional gather can have clothlikeness, thus providing a soft sense of use to a user.

According to another aspect of the present invention, the backsheet is folded up to the topsheet and the topsheet is adhered to the folding portion to form an attachment portion. This attachment portion is adhered to the topsheet. As a result, a rising edge as a root portion of the three-dimensional gather can be fixed to the topsheet.

Therefore, the three-dimensional gather is firmly raised with a sufficient height. This not only maintains the absorption performance but also provides a reliable appearance to a user.

Furthermore, since the root portion of the three-dimensional gather is fixed, expansion in the lateral direction can be prevented. Thus, the three-dimensional gather can be prevented from protruding from a conveyor line and thus can be conveyed easily.

The backsheet covers the absorbent body so as to cover from the bottom face of the absorbent body to side faces and a part of the upper face. Thus, the root portion of the three-dimensional gather can be structured by the backsheet that is a non liquid-permeable sheet in a three-dimensional manner.

This can prevent, when the absorbent article receives a pressure from a user body, body fluid pressed out of the absorbent body from being leaked or oozed from the root of the three-dimensional gather to outside.

In addition, the absorbent body is wrapped in a manner as follows. A member to be wrapped is placed on an upper face of a wrapping member to cover a bottom face and side faces of the member so as to be wrapped by the wrapping member. Then, both side sections of the wrapping member that protrude from the upper face of the member to be wrapped are folded up and are fixed to, or are made free from, the member to be wrapped. This method will be hereinafter referred to as the framing method. This method eliminates a need to structure a side flap.

Thus, the absorbent article is prevented from shrinking in the longitudinal direction. Thus, the absorbent article can be worn by a user smoothly.

According to another aspect of the present invention, not only is the three-dimensional gather composed of two layers of the backsheet and the non liquid-permeable nonwoven fabric, but the three-dimensional gather also has a free end made of a non liquid-permeable nonwoven fabric.

This not only prevents body fluid from being leaked or oozed out more securely, but also allows, even when the free end of the three-dimensional gather contacts with skin, the absorbent pad to be comfortably worn by a user without causing pricking feeling, thus reducing skin troubles.

According to another aspect of the present invention, since the skin contact surface of the folding portion is adhered with a non liquid-permeable nonwoven fabric, the backsheet that is a folding portion is prevented from having a direct contact with a human body.

This can suppress stimulation to skin when the absorbent pad is worn by a user. This not only improves the sense of use but also reduces skin troubles.

According to another aspect of the present invention, the non liquid-permeable nonwoven fabric is adhered to the backsheet at an inner side in the width direction of the folding starting point of the folding portion as an adhesion starting point.

As a result, side faces of the absorbent body are also covered by a nonwoven fabric. Thus, the backsheet is prevented from contacting with skin. This not only improves the sense of use more securely, but also reduces skin troubles.

According to another aspect of the present invention, the backsheet is provided with clothlikeness.

This not only provides, even when the backsheet is used as a skin contact surface, a soft sense of use to a user, but also enables to expect a soft sense of use visually.

According to another aspect of the present invention, the three-dimensional gather is composed of the backsheet and the topsheet covering both surfaces of the folding portion of the backsheet.

This can prevent, when the absorbent article receives a pressure from a user body, body fluid pressed out of the absorbent body from oozing from the root portion of the three-dimensional gather to outside.

Furthermore, since the folding portion of the folded backsheet is covered by the topsheet, the folding portion including the backsheet is prevented from contacting with a human body.

This suppresses stimulation to skin of a user when worn by the user.

This not only improves the sense of use, but also reduces skin trouble.

Furthermore, the three-dimensional gather is provided with clothlikeness, thus enables a user to expect a soft sense of use.

Since the root portion of the three-dimensional gather is adhered to the topsheet, the three-dimensional gather is raised firmly with a sufficient height. This not only maintains the absorption performance but also provides a reliable appearance to a user.

Since the root portion of the three-dimensional gather is fixed, expansion in the lateral direction can be prevented. Thus, the three-dimensional gather can be prevented from protruding from a conveyor line and thus can be conveyed easily without causing the products to have variation in shape.

According to another aspect of the present invention, the three-dimensional gather is composed of a non liquid-permeable backsheet and a non liquid-permeable topsheet.

This can more securely prevent the oozing of body fluid.

Furthermore, the three-dimensional gather is provided with clothlikeness, thus enables a user to expect a soft sense of use.

According to another aspect of the present invention, the backsheet folded up to the topsheet allows the backsheet to cover the absorbent body so as to cover from the bottom face of the absorbent body to side faces and a part of the upper face. This not only allows the root portion of the three-dimensional gather to be composed of the backsheet that is a non liquid-permeable sheet in a three-dimensional manner, but also allows the free end of the three-dimensional gather to be structured with a nonwoven fabric.

This can prevent pricking feeling during use and provide superior sense of use, thus preventing skin troubles.

Furthermore, when the absorbent article receives a pressure from a user body, body fluid pressed out of the absorbent body can be prevented from being leaked or oozed from the root portion of the three-dimensional gather.

Furthermore, since the three-dimensional gather is composed of two layers of the backsheet and the nonwoven fabric, the leakage or oozing of body fluid can be more securely prevented.

Furthermore, the rising edge at the root portion of the three-dimensional gather is continuously provided by the folded backsheet. This eliminates a need for providing an adhesion region to structure a rising edge for example, in the upper face of the absorbent body.

As a result, a sufficient area can be secured in the upper face of the absorbent body. Thus, when body fluid spills on the upper face of the absorbent body, the body fluid can be absorbed smoothly, thus preventing the body fluid from being leaked.

In addition, the absorbent body is wrapped in a manner as follows. A member to be wrapped is placed on an upper face of a wrapping member to cover a bottom face and side faces of the member so as to be wrapped by the wrapping member. Then, both side sections of the wrapping member that protrude from the upper face of the member to be wrapped are folded up and are fixed to, or are made free from, the member to be wrapped. This method will be hereinafter referred to as the framing method. This method eliminates a need to structure a side flap. Thus, the absorbent article is prevented from shrinking in the longitudinal direction. Thus, the absorbent article can be attached to a diaper or a diaper external member smoothly when usage.

According to another aspect of the present invention, since a nonwoven fabric is adhered to both of the backsheet and the topsheet, the nonwoven fabric can be more securely fixed to the absorbent article, and the three-dimensional gather is reinforced, thus effectiveness in leakage prevention is high.

Furthermore, since the three-dimensional gather is composed of at least two layers of the backsheet and the nonwoven fabric, the leakage or oozing of body fluid can be more securely prevented.

This also can prevent, when the absorbent article receives a pressure from a user body, body fluid pressed out of the absorbent body from being leaked or oozing from the root of the three-dimensional gather to outside.

Furthermore, since the three-dimensional gather has a free end structured with a nonwoven fabric, pricking feeling during use can be prevented, to provide superior sense of use, thus preventing skin troubles.

Furthermore, the three-dimensional gather is provided with clothlikeness, thus enables a user to expect a soft sense of use.

According to another aspect of the present invention, since the free end of the three-dimensional gather is formed from the folding starting point of a nonwoven fabric, stimulation to skin can be suppressed more effectively. This not only improves the sense of use but also suppress skin troubles further.

According to another aspect of the present invention, the three-dimensional gather is composed of the backsheet and the topsheet that covers both surfaces of the folding portion of the backsheet.

This can prevent, when the inner absorbent article receives a pressure from a user body, body fluid pressed out of the absorbent body from oozing from the root of the three-dimensional gather to outside.

Furthermore, since the folding portion of the folded backsheet is covered by the topsheet, the folding portion is prevented from having a contact with a human body.

Thus, stimulation to skin of a user when worn by the user is reduced. This not only improves the sense of use but also reduces skin trouble.

Furthermore, the three-dimensional gather is provided with clothlikeness, thus enables a user to expect a soft sense of use.

According to another aspect of the present invention, the folding portion of the backsheet includes a positioning mark in the longitudinal direction-corresponding to the positioning mark in the longitudinal direction provided on a diaper or a diaper external member, to which the inner absorbent article is attached.

Thus, the inner absorbent article can be attached to an appropriate position in the longitudinal direction of a diaper or a diaper external member in an immediate and secure manner. This not only reduces an effort when changing the inner absorbent article, but also prevents the inner absorbent article from being dislocated, thus securely preventing the leakage of body fluid.

According to another aspect of the present invention, along both side portions in the longitudinal direction of the absorbent body, an interspace is provided between the topsheet and the backsheet.

This can allow body fluid that overflowed from the absorbent body to disperse in the interspace. This not only prevents the body fluid from oozing out to outside but also improves a deodorant effect.

According to another aspect of the present invention, the backsheet is folded up to the topsheet side, and the topsheet is adhered to the folding portion to form an attachment portion. This attachment portion is adhered to the topsheet. As a result, a rising edge as the root portion of the three-dimensional gather is fixed to the topsheet.

This allows the three-dimensional gather to be raised firmly with a sufficient height. This not only maintains the absorption performance but also provides a reliable appearance to a user.

Since the root portion of the three-dimensional gather is fixed, expansion in the lateral direction is prevented. Thus, the three-dimensional gather can be prevented from protruding from a conveyor line and thus can be conveyed easily.

The backsheet covers the absorbent body so as to cover from the bottom face of the absorbent body to side faces and a part of the upper face. Thus, the root portion of the three-dimensional gather is structured with the backsheet that is a non liquid-permeable sheet, in a three-dimensional manner.

This can prevent, when the inner absorbent article receives a pressure from a user body, body fluid pressed out of the absorbent body from being leaked or oozing from the root of the three-dimensional gather to outside.

In addition, the absorbent body is wrapped in a manner as follows. A member to be wrapped is placed on an upper face of a wrapping member to cover a bottom face and side faces of the member so as to be wrapped by the wrapping member. Then, both side sections of the wrapping member that protrude from the upper face of the member to be wrapped are folded up and are fixed to, or are made free from, the member to be wrapped. This method will be hereinafter referred to as the framing method. This method eliminates a need to structure a side flap.

Thus, the absorbent article is prevented from shrinking in the longitudinal direction. Thus, the absorbent article can be attached to a diaper or a diaper external member smoothly when usage.

According to another aspect of the present invention, the three-dimensional gather is composed of the backsheet and the topsheet that covers both surfaces of the folding portion of the backsheet.

This can prevent, when the inner absorbent article receives a pressure from a user body, body fluid pressed out of the absorbent body from oozing from the root of the three-dimensional gather to outside.

Furthermore, since the folding portion of the folded backsheet is covered by the topsheet, the folding portion including the folded backsheet is prevented from having a contact with a human body.

This suppresses stimulation to skin of a user when worn by the user. This not only improves the sense of use but also prevents skin trouble.

Furthermore, the three-dimensional is provided with cloth-likeness, thus enables a user to expect a soft sense of use.

Since the root portion of the three-dimensional gather is adhered to the topsheet, the three-dimensional gather is raised firmly with a sufficient height. This not only maintains the absorption performance but also provides a reliable appearance to a user.

Since the root portion of the three-dimensional gather is fixed, expansion in the lateral direction is prevented. Thus, variation in shape of the products due to the three-dimensional gather protruding from a conveyor line can be prevented, thus providing an easy conveyance.

EMBODIMENT 1

Hereinafter, Embodiment 1 of the present invention will be described in detail with reference to figures.

This Embodiment will exemplarily describe an absorbent pad that can be used as an absorbent article that is directly attached to an underwear such as a sanitary napkin, or as an inner absorbent article attached to a diaper or a diaper external member such as an urine absorption pad.

Figure 1:
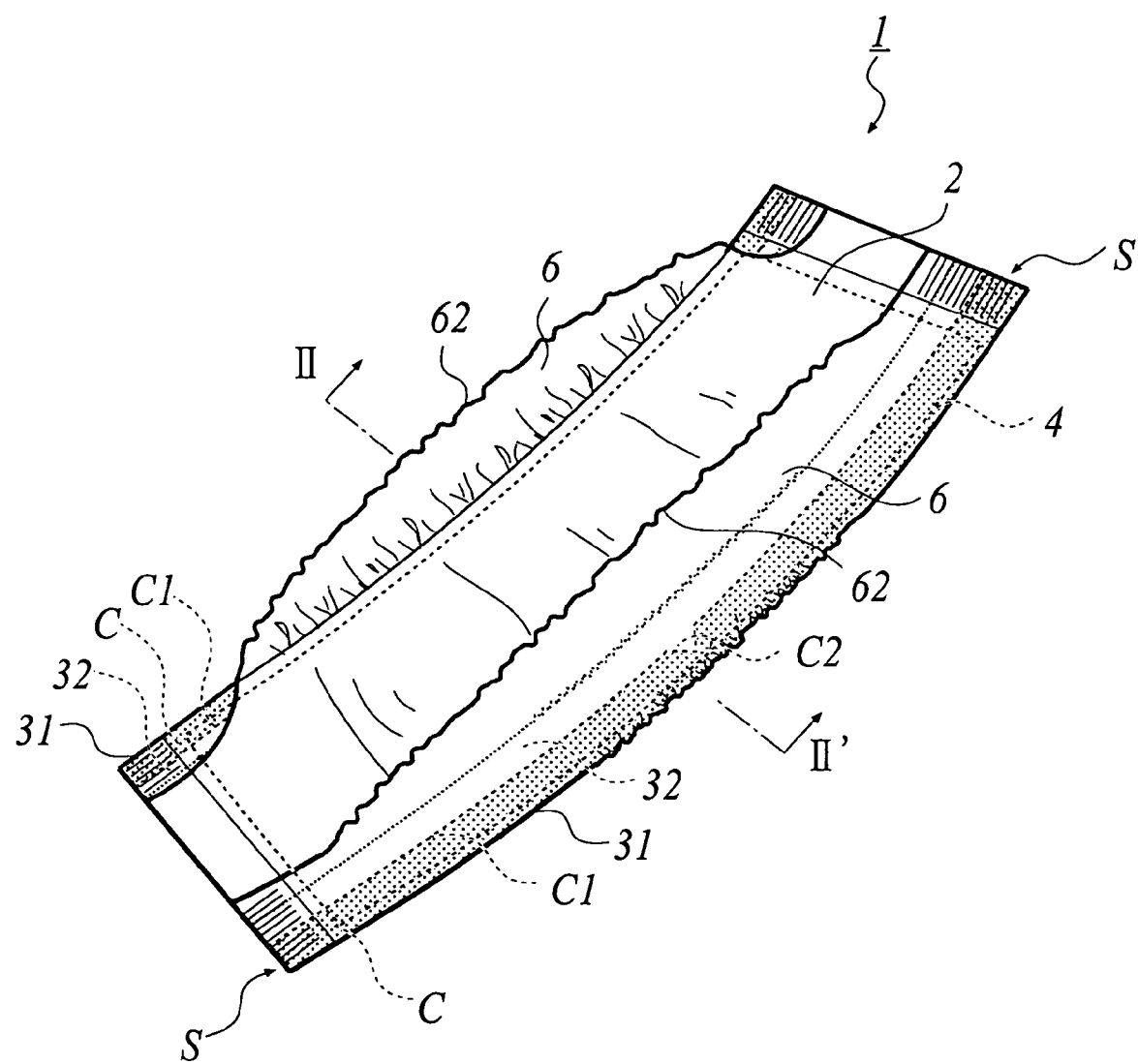
[FIG. 1] This is a development view of an absorbent pad of Embodiment 1 using an absorbent article of the present invention.
Figure 2:
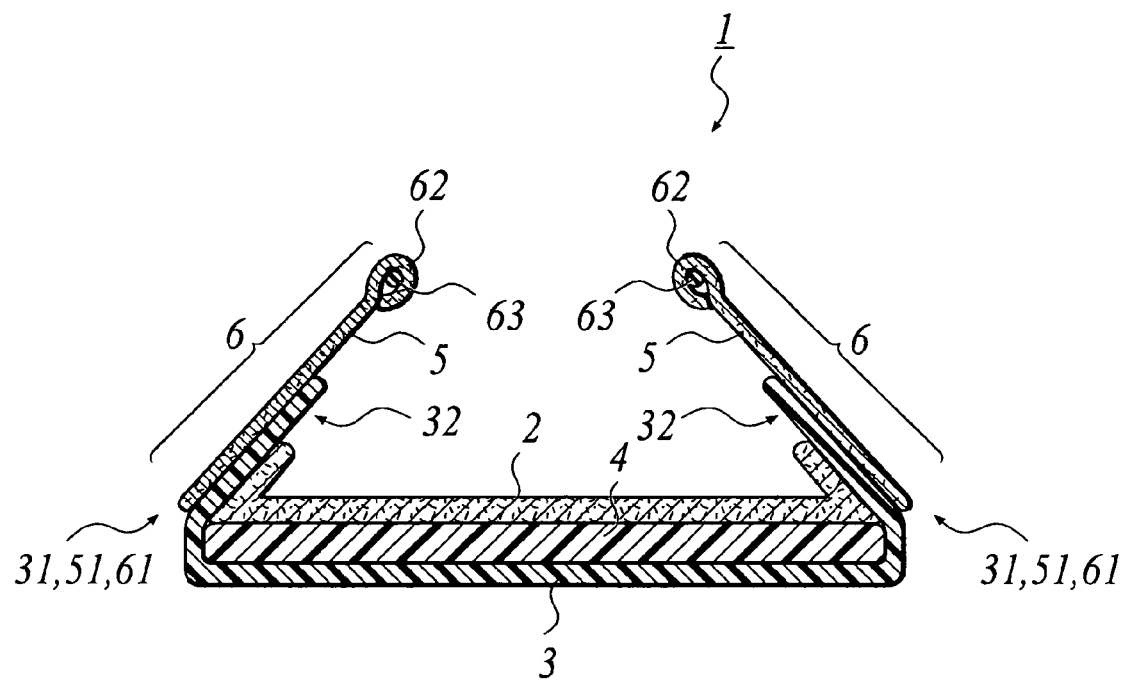
[FIG. 2] This is a cross-sectional view taken at II-II' of FIG. 1.

FIG. 1 is a development view illustrating an absorbent pad of Embodiment 1 applied with the absorbent article or the inner absorbent article of the present invention. FIG. 2 is a cross-sectional view taken at II-II' of FIG. 1.

As shown in FIGS. 1 and 2, an absorbent pad 1 comprises a liquid-permeable topsheet 2 provided at a contact face that contacts with a human body, a non liquid-permeable backsheet 3 provided at a surface opposite to the topsheet 2 and provided outside when the absorbent pad 1 is worn by a user, an absorbent body 4 provided between the topsheet 2 and the backsheet 3, and the like.

The topsheet 2 is a liquid-permeable nonwoven fabric that is shaped to cover a surface of the absorbent body 4 (surface having a contact with skin).

As for material used for nonwoven fabric that comprise the topsheet 2, natural fiber or synthetic fiber can be used. Natural fiber includes cotton, cellulose (wood pulp), wool, or silk for example. Synthetic fiber may include, for example, polypropylene (PP), polyethylene (PE), nylon, polyester (PET), or acryl. Synthetic fiber may also include PE/PP-mixed nonwoven fabric, PE/PET-mixed nonwoven fabric, or bicomponent fiber (mixed fiber) obtained by appropriately combining the above materials.

Concerning a method for manufacturing a nonwoven fabric from these fibrous materials, known methods can be appropriately used, including, for example, chemical bond, thermal bond, or spun lace. Synthetic fiber for example, may be manufactured by an arbitrary method such as spun bond method, melt blow method, or a combination of these methods with the above adhesion method.

The backsheet 3 is formed by a sheet material at least having a water-shielding characteristic such as polyethylene and the like. The backsheet 3 is preferably formed by a sheet material having a moisture permeability from the viewpoint of preventing stuffiness. A preferable sheet material having these water shielding characteristic and moisture permeability is a microporous sheet material obtained by melting and mixing inorganic filling agent into olefin-base resin such as polyethylene, polypropylene, and the like to form a sheet, and then subsequently drawing the sheet in a uniaxial or biaxial direction.

To a surface of the backsheet 3 that is to contact with underwear, an adhesive layer (not shown) is provided. This adhesive layer can fix the absorbent pad 1 to prevent the absorbent pad 1 from being dislocated from the underwear, a diaper, or an external member of the diaper when used.

The backsheet 3 covers a bottom face of the absorbent body 4 and further covers side faces of the absorbent body 4. The backsheet 3 is folded up to the topsheet 2 at both side portions in the longitudinal direction of the upper face of the absorbent body 4, from a folding starting point 31 as a starting point, thereby forming a folding portion 32.

The backsheet 3 and the topsheet 2 are adhered to each other in the vicinity of the folding starting point 31 by a hotmelt adhesive agent or the like.

To the opposite surfaces of the folding portions 32, 32 of the backsheet 3 that face the topsheet 2, regions colored with a predetermined color, that is, colored regions C, C, are provided. Specifically, as shown in FIG. 1, the colored regions C are provided from the folding starting point 31 of the folding portion 32 to colored end portions C1 at predetermined positions at inner sides in the width direction of the folding portions 32, for example. Furthermore, colored notched portions C2 that are substantially V-like shaped, are provided at predetermined positions at inner sides in the longitudinal direction of the colored regions C, in a direction from the colored end portions C1 to the folding starting points 31. The colored regions C, the colored end portions C1, and the colored notched portions C2 at the folding portions 32 can be visually recognized from a side of which the absorbent pad 1 comes in contact with a skin. The colored end portions C1 function as positioning marks in the width direction corresponding to positioning marks in the width direction provided on a diaper or a diaper external member (not shown) to which the absorbent pad 1 as an inner absorbent article is attached. Thus, the colored end portion C1 is positioned so as to correspond to a positioning mark in the width direction provided on a diaper or a diaper external member (not shown). The colored notched portion C2 functions as a positioning mark in the longitudinal direction corresponding to a positioning mark in the longitudinal direction provided in a diaper or a diaper external member (not shown) to which the absorbent pad 1 is attached. Thus, position or number of the colored notched portions C2 are determined based on positioning mark(s) provided on a diaper or a diaper external member (not shown). The shape of the colored notched portion C2 is not particularly limited.

Furthermore, the positioning mark in the longitudinal direction is not limited to the colored notched portion C2 and may also be provided by printing or adhesion of another member.

The absorbent body 4 is structured, for example, by covering an absorbent body core (not shown) with a liquid-permeable crepe paper (not shown). The absorbent body core is formed by combining an absorbent material such as cotton, pulp, or the like, and a sheet-like base such as fiber, film, or the like, with a superabsorbent resin such as superabsorbent polymer. The absorbent body core may have a single layer structure or may have a structure having a plurality of layers.

Next, three-dimensional gathers 6, 6 will be described. The three-dimensional gather 6 is formed by adhering a gather sheet 5 made of nonwoven fabric to the folding portion 32 of the backsheet 3. Specifically, the three-dimensional gather 6 is formed, as shown in FIG. 2, by adhering the gather sheet 5 to a surface opposite to the surface of the folding portion 32 that face the topsheet 2, from the folding starting point 31 to an end portion of the folding portion 32.

In addition, the three-dimensional gather 6 is provided with an elastic member 63 in the longitudinal direction, thus the three-dimensional gather 6 is elastically formed in the longitudinal direction.

The three-dimensional gather 6 has a rising edge 61 that is provided at the same position to the folding starting point 31 of the backsheet 3 and is also the same position to the adhesion starting point 51 of the gather sheet 5. Thus, the vicinity of the root portion of the rising edge 61 of the three-dimensional gather 6 is composed of two layers of the backsheet 3 and the gather sheet 5.

On the other hand, the gather sheet 5 is provided to protrude from the folding portion 32. Thus, the vicinity of a free end 62 of the three-dimensional gather 6 is composed of only one layer of the gather sheet 5.

In other words, the rising edge 61 at the root portion of the three-dimensional gather 6 is composed of the backsheet 3 and the gather sheet 5. The vicinity of the free end 62 of the three-dimensional gather 6 that particularly contacts with (i.e., that is rubbed with) skin during the usage is composed of only the gather sheet 5.

Furthermore, as shown in FIG. 1, the three-dimensional gather 6 is provided substantially along both side portions in the longitudinal direction of the absorbent body 4 without the free end 62 being fixed. However, at both end portions S, S in the longitudinal direction of the absorbent pad 1, the respective free ends 62 of the three-dimensional gathers 6 are directly folded up to the topsheet 2 and are fixed to the topsheet 2.

The gather sheet 5 is desirably made of a nonwoven fabric through which liquid is hard to permeate, and may be made of a nonwoven fabric in a single layer or may be made of a nonwoven fabric in a layered structure.

Nonwoven fabric through which liquid is hard to permeate includes, for example, spunbond nonwoven fabric; laminated spunbond nonwoven fabric, melt-blown nonwoven fabric, spunbond nonwoven fabric; laminated spunbond nonwoven fabric, melt-blown nonwoven fabric, melt-blown nonwoven fabric, spunbond nonwoven fabric; heat roll nonwoven fabric; non liquid-permeable nonwoven fabric; or air through nonwoven fabric.

As for adhesive used to adhere the gather sheet 5 to the backsheet 3, adhesive may be appropriately selected from, for example, ethylene-vinyl acetate copolymer resin (EVA; Ethylene Vinyl Acetate), polyvinyl alcohol (PVA), acrylamide polyvinyl alcohol copolymer, acrylic acid ester, vinyl acetate copolymer, carboxymethyl cellulose sodium, styrene-based elastomer (e.g., SIS, SBS, SIBS, SEPS), polyester acrylic elastomer, or polyolefin-based elastomer.

Adhesive may be coated, for example, by well-known methods such as curtain method, beat method, slot method, or spiral method (e.g., spray coating, blade coating).

According to the absorbent pad 1 according to Embodiment 1, the free end 62 of the three-dimensional gather 6 made of a nonwoven fabric prevents, even when the three-dimensional gather 6 contacts with a human body during usage, pricking feeling and thus sense of use can be improved and skin troubles can be avoided.

Furthermore, the backsheet 3 folded up to the topsheet 2 allows the backsheet 3 to cover the absorbent body 4 so as to cover from the bottom face of the absorbent body 4 to the side faces and a part of the upper face, thus providing a structure where the rising edge 61 at the root portion of the three-dimensional gather 6 is composed of the backsheet 3 made of a non liquid-permeable sheet, in a three-dimensional manner.

Therefore, body fluid pressed out of the absorbent body 4 is prevented from oozing from the root portion of the three-dimensional gather 6 to outside, when the absorbent pad 1 receives a pressure from a user body.

Furthermore, since the three-dimensional gather 6 is composed of two layers of the backsheet 3 and the nonwoven fabric, body fluid can be prevented from oozing out with higher security.

Furthermore, the rising edge 61 as the root portion of the three-dimensional gather 6 is continuously formed by the folded backsheet 3, thus eliminating a need for forming an adhesion region to provide the rising edge 61 at the upper face of the absorbent body 4. Thus, the upper face of the absorbent body 4 can secure a sufficient water-absorbing area. As a result, body fluid can be absorbed smoothly, preventing the body fluid from being leaked.

Furthermore, the nonwoven fabric adhered to a surface contacts with skin and is at an opposite side of a surface that face the topsheet 2 of the folded backsheet 3 can prevent the folded backsheet 3 from contacting with a human body. This can suppress stimulation to a skin when worn by a user. This not only improves the sense of use but also prevents skin troubles.

Furthermore, since the absorbent body 4 covered by a method called the framing method, a need for providing a side flap 42 is eliminated. This prevents the absorbent pad 1 from shrinking in the longitudinal direction. Thus, the absorbent pad can be smoothly attached to an underwear, a diaper, or a diaper external member (not shown) for use.

Furthermore, the colored region C and the colored notched section C2 are provided at the folding section 32 of the backsheet 3 so as to correspond to the positioning mark in the width direction and the positioning mark in the longitudinal direction that are provided on a diaper or a diaper external member (not shown) to which the absorbent pad 1 is attached. This enables immediate and secure attachment of the absorbent pad 1 to appropriate positions in the width direction and the longitudinal direction of a diaper or a diaper external member (not shown). This not only reduces an effort when changing the absorbent pad 1, but also prevents the absorbent pad 1 from being dislocated from an appropriate position, thus securely preventing the leakage of body fluid.

EMBODIMENT 2

Next, the absorbent pad 100 according to Embodiment 2 will be described with reference to FIG. 3.

Figure 3:
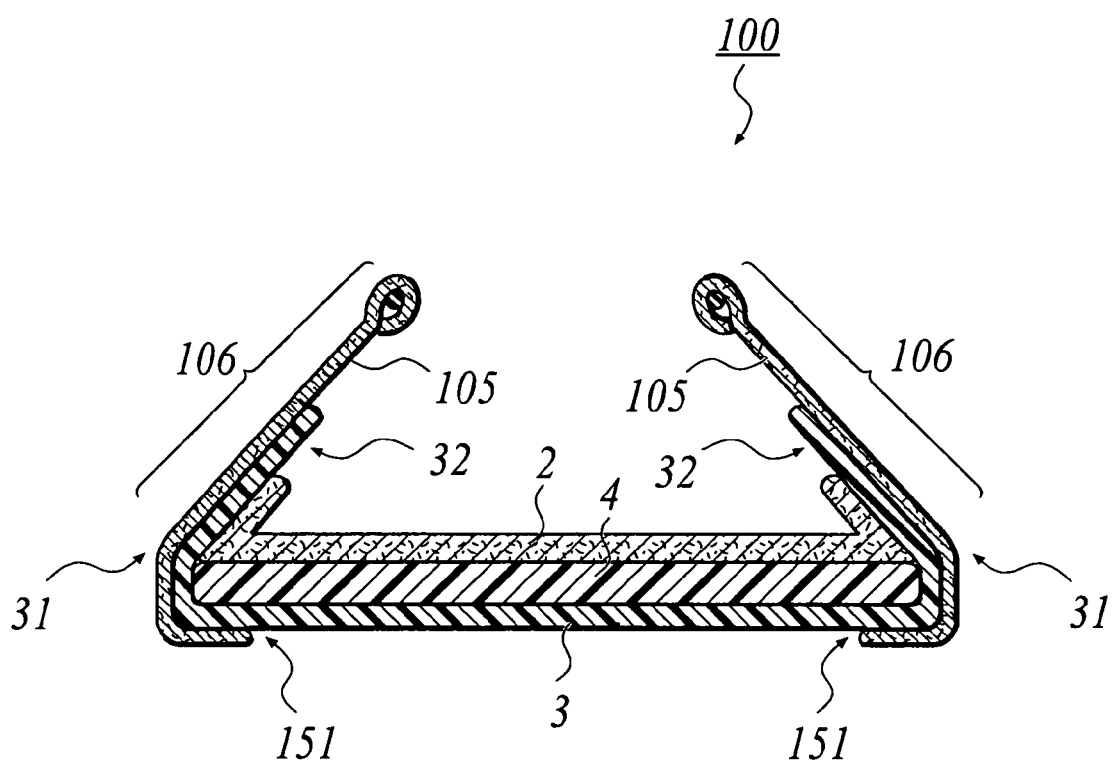
[FIG. 3] This is a cross-sectional view illustrating a part corresponding to II-II' of FIG. 1 of Embodiment 1 in an absorbent pad of Embodiment 2 using the absorbent article of the present invention.

FIG. 3 is a cross-sectional view illustrating the absorbent pad of Embodiment 2 of the present invention.

An absorbent body pad 100 shown in FIG. 3 has a gather sheet 105 different from that of the absorbent pad 1 of Embodiment 1. Thus, Embodiment 2 will be described so that the same components as those of Embodiment 1 have the same reference numerals and will not be described further.

As shown in FIG. 3, gather sheets 105 forming three-dimensional gathers 106, 106 of the absorbent pad 100 completely cover the folding portions 32 of the backsheet 3 so as to cover the side faces of the absorbent body 4. The adhesion starting point 151 is adhered to the backsheet 3 so as to be positioned at the bottom face of the absorbent body 4. That is, the adhesion starting point 151 is adhered to the backsheet 3 so that the adhesion starting point 151 is at the inner side in the width direction than the folding starting point 31 of the folding portion 32. Thus, when compared with Embodiment 1, Embodiment 2 provides a much larger area in which the gather sheet 105 is adhered to the backsheet 3, thus providing a sufficient adhesion area.

According to the absorbent pad 100 of Embodiment 2 as described above, the gather sheet 105 can be adhered to the backsheet 3 with a sufficient area. This can more effectively prevent the leakage or oozing of body fluid and can completely prevent the backsheet 3 from contacting with skin. Therefore, not only the sense of use is improved, but skin troubles are also prevented.

EMBODIMENT 3

Next, an absorbent pad 200 according to Embodiment 3 will be described with reference to FIG. 4.

Figure 4:
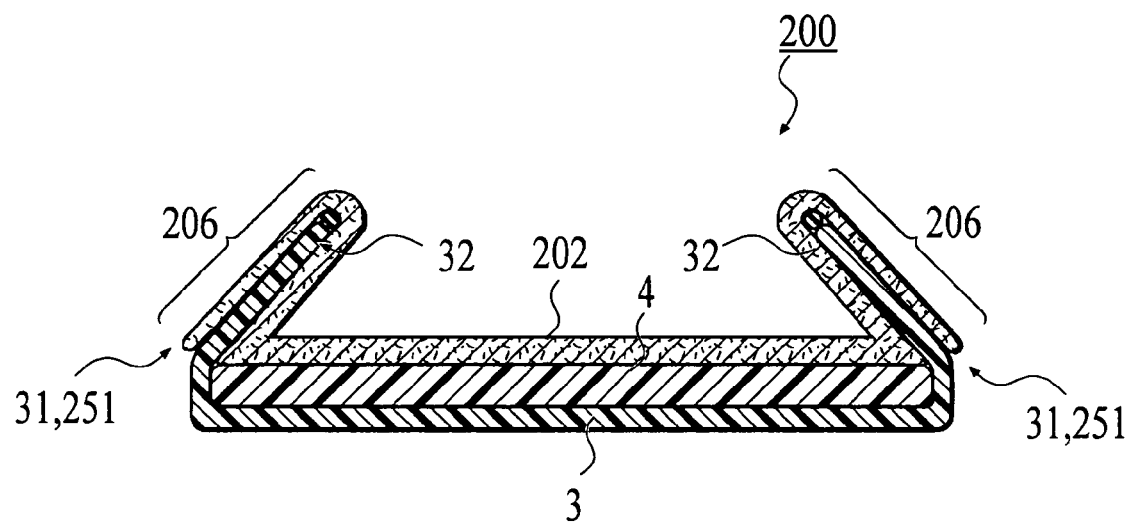
[FIG. 4] This is a cross-sectional view illustrating a part corresponding to II-II' of FIG. 1 of Embodiment 1 in an absorbent pad of Embodiment 3 using the absorbent article of the present invention.

FIG. 4 is a cross-sectional view illustrating the absorbent pad of Embodiment 3 of the present invention.

The absorbent pad 200 shown in FIG. 4 has a topsheet 202 that is different from that of the absorbent pad 1 of Embodiment 1. Thus, Embodiment 3 will be described so that the same components as those of Embodiment 1 have the same reference numerals and will not be described further.

As shown in FIG. 4, three-dimensional gathers 206, 206 of the absorbent pad 200 are composed of a topsheet 202 and the backsheet 3. The backsheet 3 covers the bottom face of the absorbent body 4 and further covers side faces of the absorbent body 4 and is folded up to the topsheet 202 at both side portions in the longitudinal direction of the upper face of the absorbent body 4 from the folding starting point 31 as a starting point, thereby forming the folding portion 32.

On the other hand, both surfaces of the folding portion 32 of the backsheet 3 folded up to the topsheet 202 are entirely covered by the topsheet 202 and the folding starting point 31 functions as an adhesion starting point 251, thereby providing the three-dimensional gather 206.

That is, the three-dimensional gather 206 is composed of three layers of the backsheet 3 and the topsheets 202 sandwiching from the both surfaces of the backsheet 3.

In this structure, a region of the topsheet 202 that is covering the upper face of the absorbent body 4 (i.e., body fluid absorption region) is liquid-permeable and a region forming the three-dimensional gather 206 is less liquid-permeable than the body fluid absorption region. Specifically, the region of the topsheet 202 forming the three-dimensional gather 206 is applied with a water repellant treatment or waterproof treatment for example. The region forming the three-dimensional gather 206 is not limited to the less liquid-permeable one and also may be non liquid-permeable.

A liquid-permeable nonwoven fabric forming the body fluid absorption region may be the one included in the list of nonwoven fabrics for the description of the topsheet 2.

According to the absorbent pad 200 of Embodiment 3, the three-dimensional gather 206 is composed of the backsheet 3 and the topsheets 202 entirely covering both surfaces of the backsheet 3. This can prevent body fluid pressed out of the absorbent body 4 from oozing from the root portion of the three-dimensional gather 206 to outside, when the absorbent pad 200 receives a pressure from a user body.

Furthermore, the folded backsheet 3 entirely covered by the topsheet 202 prevents the folded backsheet 3 from contacting with a human body, thus suppressing stimulation to skin of a user when worn by the user. This not only improves the sense of use but also prevents skin troubles.

Furthermore, the three-dimensional gather 206 can have clothlikeness, thus providing a soft sense of use to a user.

Furthermore, oozing of body fluid can be more securely prevented by the three-dimensional gather 206 composed of the non liquid-permeable backsheet 3 and a region of the topsheet 202 that is less liquid-permeable than a region positioned at the upper face of the absorbent body 4.

EMBODIMENT 4

Next, an absorbent pad 300 will be described with reference to FIG. 5.

Figure 5:
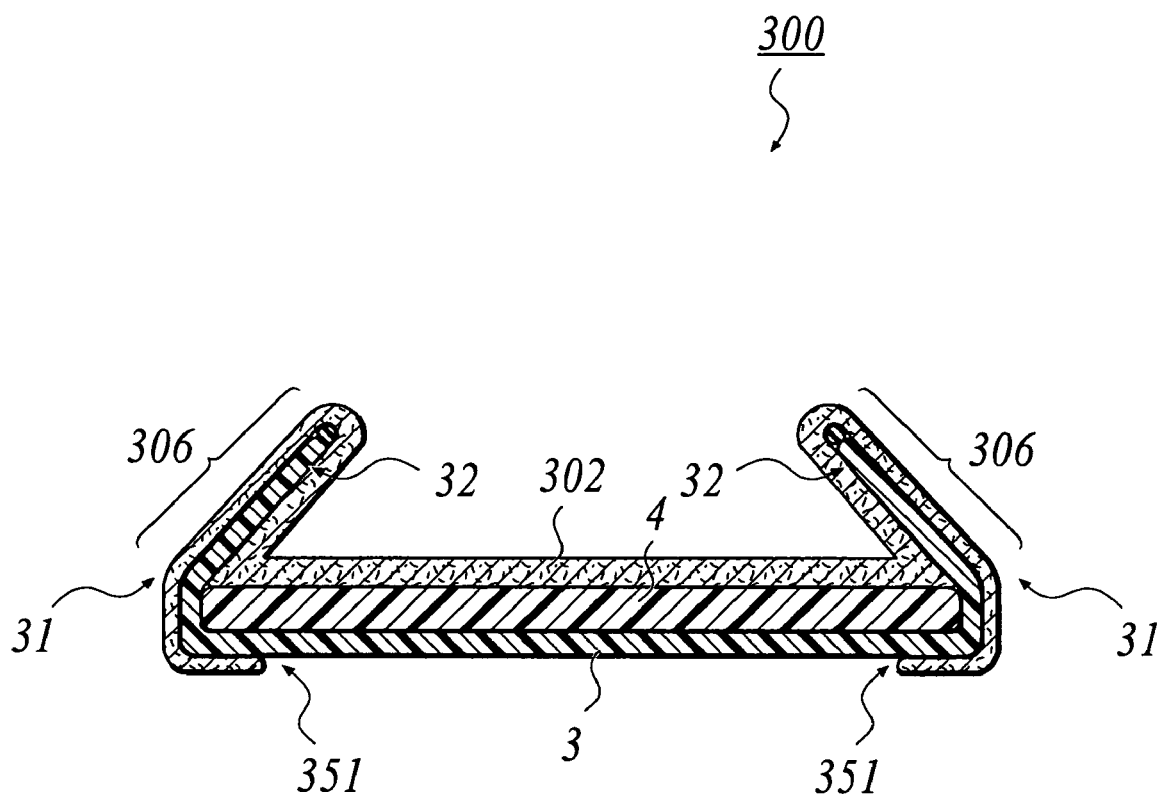
[FIG. 5] This is a cross-sectional view illustrating a part corresponding to II-II' of FIG. 1 of Embodiment 1 in an absorbent pad of Embodiment 4 using the absorbent article of the present invention.

FIG. 5 is a cross-sectional view illustrating an absorbent pad of Embodiment 4 of the present invention.

The absorbent pad 300 shown in FIG. 5 has a topsheet 302 that is different from that of the absorbent pad 200 of Embodiment 3. Thus, Embodiment 4 will be described so that the same components as those of Embodiment 3 have the same reference numerals and will not be described further.

As shown in FIG. 5, the absorbent pad 300 has three-dimensional gathers 306, 306 composed of a topsheet 302 and a backsheet 3. The backsheet 3 covers the bottom face of the absorbent body 4 and also covers the side faces of the absorbent body 4. The backsheet 3 is folded up to the topsheet 302 at both side portions in the longitudinal direction of the upper face of the absorbent body 4 from the folding starting point 31 as a starting point, thereby forming the folding portion 32.

On the other hand, both surfaces of the folding portion 32 of the backsheet 3 fold up to the topsheet 302 are entirely covered by the topsheet 302 and the side face of the absorbent body 4 is also covered by the topsheet 302. An adhesion starting point 351 is provided on the backsheet 3 covering the bottom face of the absorbent body 4, thereby providing the three-dimensional gather 306.

In other words, the three-dimensional gather 306 is composed of three layers of the backsheet 3 and the topsheets 302 sandwiching from the both surfaces of the backsheet 3.

In this structure, a region of the topsheet 302 that covers the upper face of the absorbent body 4 (i.e., body fluid absorption region) is liquid-permeable and a region forming the three-dimensional gather 306 is less liquid-permeable than the body fluid absorption region. Specifically, the region of the topsheet 302 forming the three-dimensional gather 306 is applied with a water repellant treatment or waterproof treatment for example. As for liquid-permeable nonwoven fabric, nonwoven fabrics listed for the description of the topsheet 2 may be used.

According to the absorbent pad 300 of Embodiment 4, an adhesion region of the topsheet 302 and the backsheet 3 that compose the three-dimensional gather 306 can be enlarged, thus preventing the leakage or oozing of body fluid more effectively.

EMBODIMENT 5

Next, an absorbent pad 400 according to Embodiment 5 will be described with reference to FIG. 6.

Figure 6:
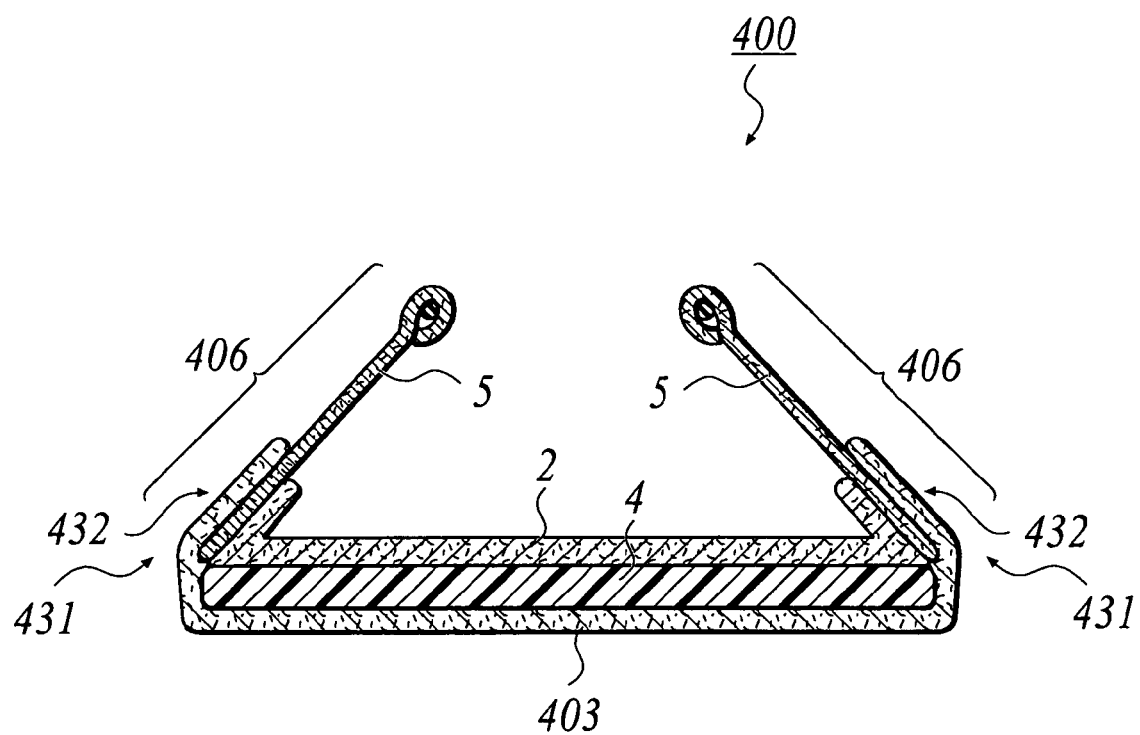
[FIG. 6] This is a cross-sectional view illustrating a part corresponding to II-II' of FIG. 1 of Embodiment 1 in an absorbent pad of Embodiment 5 using the absorbent article of the present invention.

FIG. 6 is a cross-sectional view illustrating the absorbent pad 400 of Embodiment 5 of the present invention.

The absorbent pad 400 shown in FIG. 6 has the topsheet 2 and the gather sheet 5 with the same shapes as those of Embodiment 1, however, has a different arrangement of sheets compared to that of Embodiment 1, concerning forming of a backsheet 403 and a three-dimensional gather 406. Thus, Embodiment 5 will be described so that the same components as those of Embodiment 1 have the same reference numerals and will not be described further.

As shown in FIG. 6, the absorbent pad 400 has three-dimensional gathers 406, 406 composed of the backsheet 403 and the gather sheet 5. In this Embodiment, the gather sheet 5 is adhered to a surface of a folding portion 432 that faces the topsheet 2, wherein the folding portion 432 is formed by the backsheet 403 folded from a folding starting point 431 as a starting point. In particular, the gather sheet 5 is adhered to the backsheet 403 from the folding starting point 431 to the folding portion 432, thereby providing the three-dimensional gather 406.

In the above structure, the backsheet 403 is composed of a non liquid-permeable film layer or a ramie nonwoven fabric including a breathable nonwoven fabric layer.

Here, the term "ramie nonwoven fabric" means, a nonwoven fabric called a laminate nonwoven fabric in which a nonwoven fabric is layered on a polyethylene sheet for example.

Next, an example of a method for manufacturing the absorbent pad 400 will be described with reference to FIG. 7.

Figure 7:
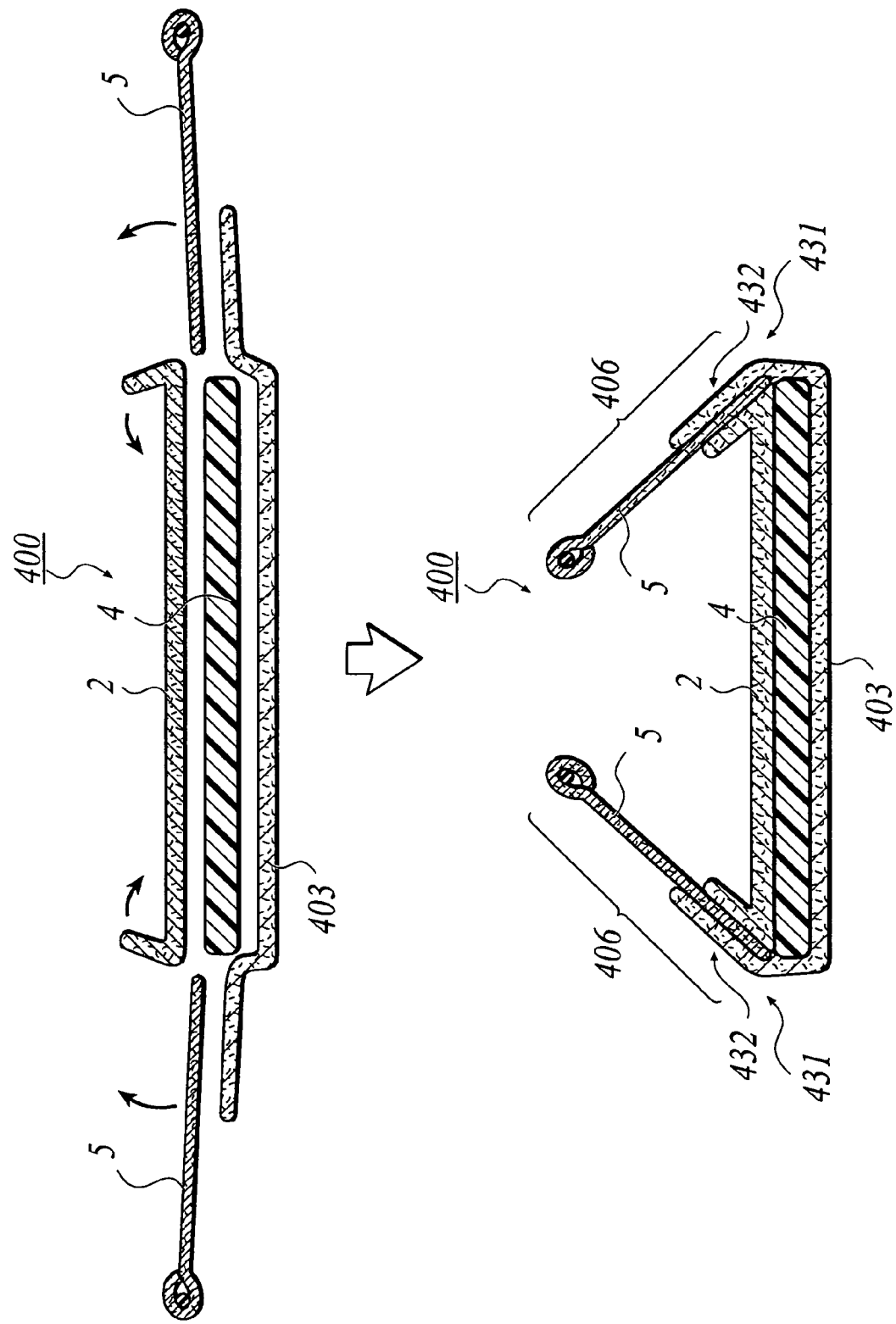
[FIG. 7] This illustrates a method for manufacturing the absorbent pad of FIG. 6.

FIG. 7 illustrates the method for manufacturing the absorbent pad 400.

As shown in FIG. 7, the absorbent body 4 is placed on the upper face of the backsheet 403, and the topsheet 2 is placed on its upper face. Further, the gather sheets 5 are provided on the upper face of the topsheet 2, where is also the upper face of the backsheet 403 positioned in exterior to the left and right side portions in the longitudinal direction of the topsheet 2. Here, the topsheet 2 has a length in the lateral direction (width) that is shorter than the length of the backsheet 403 in the lateral direction (width). Thus, the backsheet 403 has a direct contact with the gather sheets 5 at both end portions in the width direction of the backsheet 403 (i.e., both side portions in the longitudinal direction).

Next, both side portions in the longitudinal direction of the topsheet 2 are folded up in the direction along which the gather sheets 5 are provided (upper face direction). At the same time, within the backsheet 403 and the gather sheets 5 being overlapped, they are fold up from the folding starting point 431 as a starting point, thereby forming the folding portions 432. Subsequently, the folding portions 432 are fixed to the gather sheets 5, thereby providing the three-dimensional gather 406.

According to the absorbent pad 400 of Embodiment 5 as described above, the backsheet 403 using a ramie nonwoven fabric provides clothlikeness to the backsheet 403, thus providing a soft sense of use to a user.

EMBODIMENT 6

Next, an absorbent pad 500 according to Embodiment 6 will be described with reference to FIG. 8.

Figure 8:
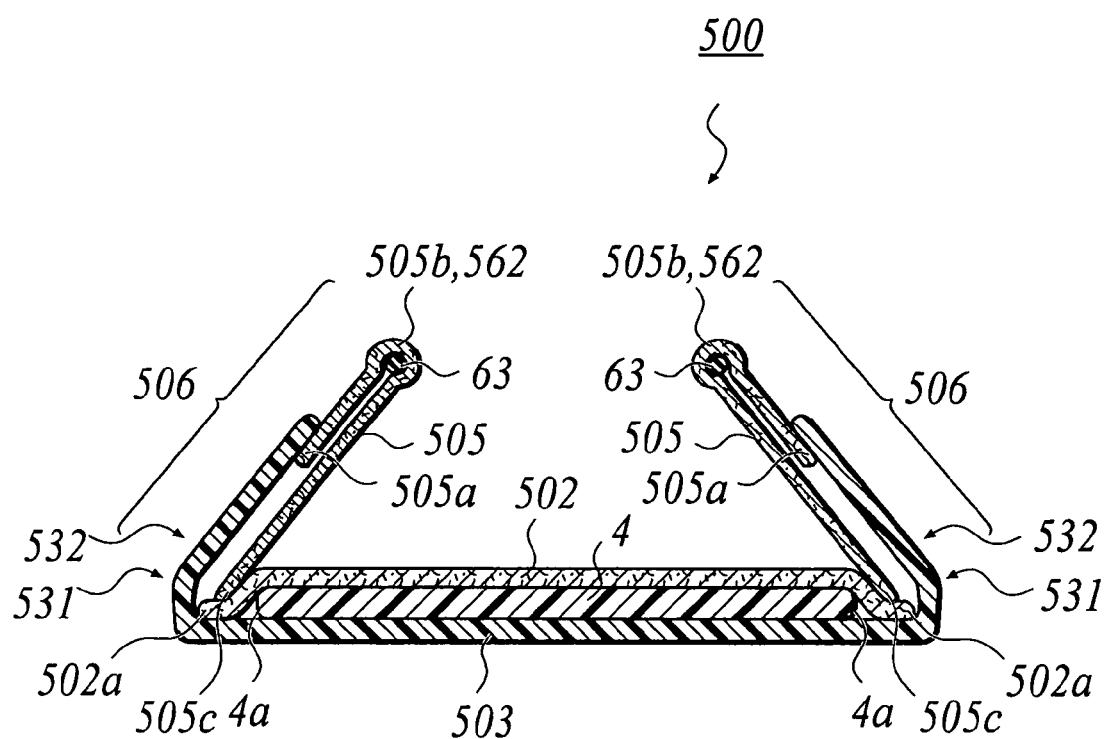
[FIG. 8] This is a cross-sectional view illustrating a part corresponding to II-II' of FIG. 1 of Embodiment 1 in an absorbent pad of Embodiment 6 using the absorbent article of the present invention.

FIG. 8 is a cross-sectional view illustrating the absorbent pad 500 of Embodiment 6 of the present invention.

The absorbent pad 500 shown in FIG. 8 is different from that of Embodiment 1 in the shapes of a topsheet 502, a backsheet 503, and a gather sheet 505, and the arrangement of the respective sheets for providing a three-dimensional gather 506. Thus, Embodiment 6 will be described so that the same components as those of Embodiment 1 have the same reference numerals and will not be described further.

As shown in FIG. 8, the absorbent pad 500 has the three-dimensional gathers 506, 506 comprising the topsheet 502, the backsheet 503, and the gather sheets 505. In this Embodiment, the backsheet 503 includes, for example, a non liquid-permeable film layer. The topsheet 502 covers both side portions 4a, 4a in the longitudinal direction of the absorbent body 4. Both side portions 502a, 502a in the longitudinal direction of the topsheet 502 are fixed to the backsheet 503. The gather sheet 505 is folded up from a folding starting point 505b as a starting point. The folding starting point 505b forms a free end 562 of the three-dimensional gather 506. An end portion 505a (one end portion) fold up to the backsheet 503 of the gather sheet 505 is adhered to a surface of the backsheet 503 that faces the topsheet 502 of the folding portion 532 folded up from the folding starting point 531 as a starting point. Furthermore, an end portion 505c (the other end section) fold up to the topsheet 502 of the gather sheet 505, and a portion in the vicinity thereof are adhered to a surface that face the folding portion 532 of the backsheet 503 of the topsheet 502 covering a side portion 4a in the longitudinal direction of the absorbent body 4. Thus the three-dimensional gather 506 is provided. The folding starting point 505b of the gather sheet 505 includes an elastic member 63.

According to the absorbent pad 500 of Embodiment 6 as described above, since the gather sheets 505 are adhered to both of the backsheet 503 and the topsheet 502, the gather sheets 505 and the absorbent pad 500 can be fixed more securely, thus reinforcing the three-dimensional gather 506 to provide high efficiency to prevent leakage.

Furthermore, the root portion of the three-dimensional gather 506 composed of the backsheet 503, the gather sheet 505, and the topsheet 502 can more securely prevent body fluid from being leaked or oozed out.

Furthermore, body fluid pressed out of the absorbent body 4 can be prevented from being leaked or oozed from the root portion of the three-dimensional gather 506 to outside when the absorbent pad 500 receives a pressure from a user body.

Furthermore, the free end 562 of the three-dimensional gather 506 is composed of folding starting point 505b of the nonwoven fabric through which liquid is difficult to permeate. Thus, stimulation to skin can be suppressed when the absorbent pad is worn by a user. This not only improves the sense of use but also reduces skin troubles.

Furthermore, the three-dimensional gather 506 is provided with clothlikeness, thus providing a soft sense of use to a user.

It is noted that the gather sheet 505 may not have the folding starting point 505b, provided in an obvious manner.

Figure 9:
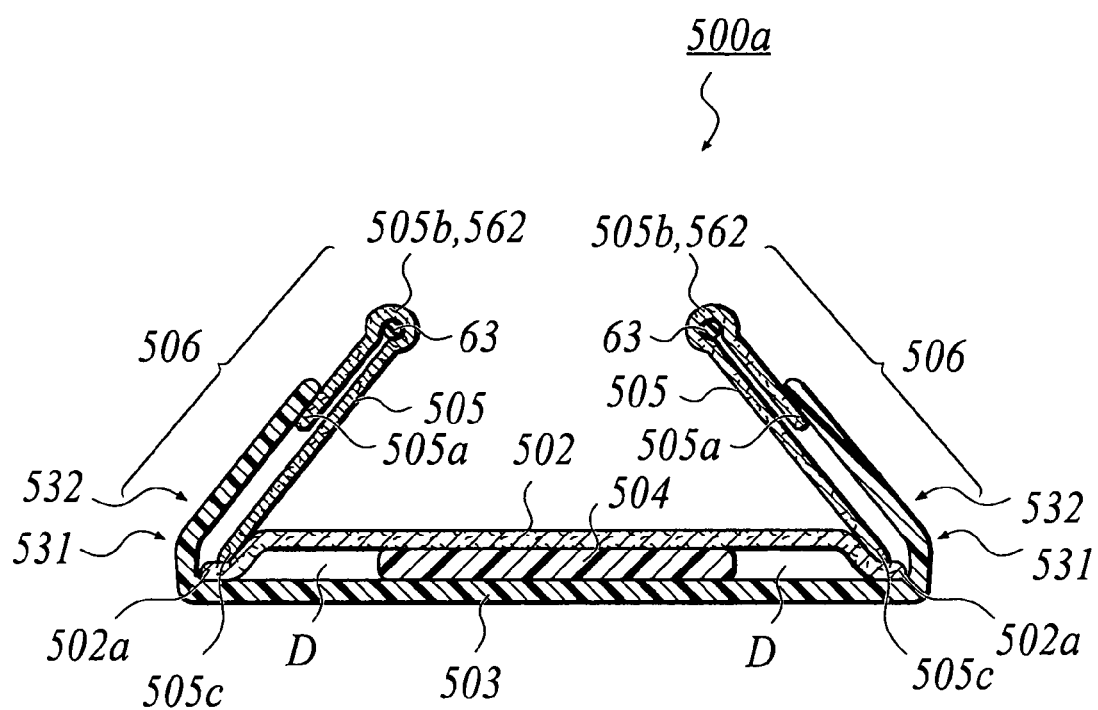
[FIG. 9] This is a cross-sectional view illustrating a modification of the absorbent pad of Embodiment 6 using the absorbent article of the present invention.

Alternatively, the absorbent pad 500 may be provided as in the absorbent pad 500a shown in FIG. 9. Specifically, the absorbent body 504 may have a width smaller than that of the absorbent body 4 of the absorbent pad 500 and interspaces D, D may be provided between the topsheet 502 and the backsheet 503 along the longitudinal direction of both side portions in the longitudinal direction of the absorbent body 504.

This allows body fluid that overflowed from the absorbent body 504 to disperse in the interspaces D, D. This not only prevents the body fluid from oozing out to outside but also improves a deodorant effect.

EMBODIMENT 7

Hereinafter, Embodiment 7 of the present invention will be described in detail with reference to figures.

Embodiment 7 will be described by, for example, an absorbent article directly attached to an underwear (such as sanitary napkin) or an inner absorbent article attached to a diaper or a diaper external member for use (such as urine absorption pad).

Figure 10:
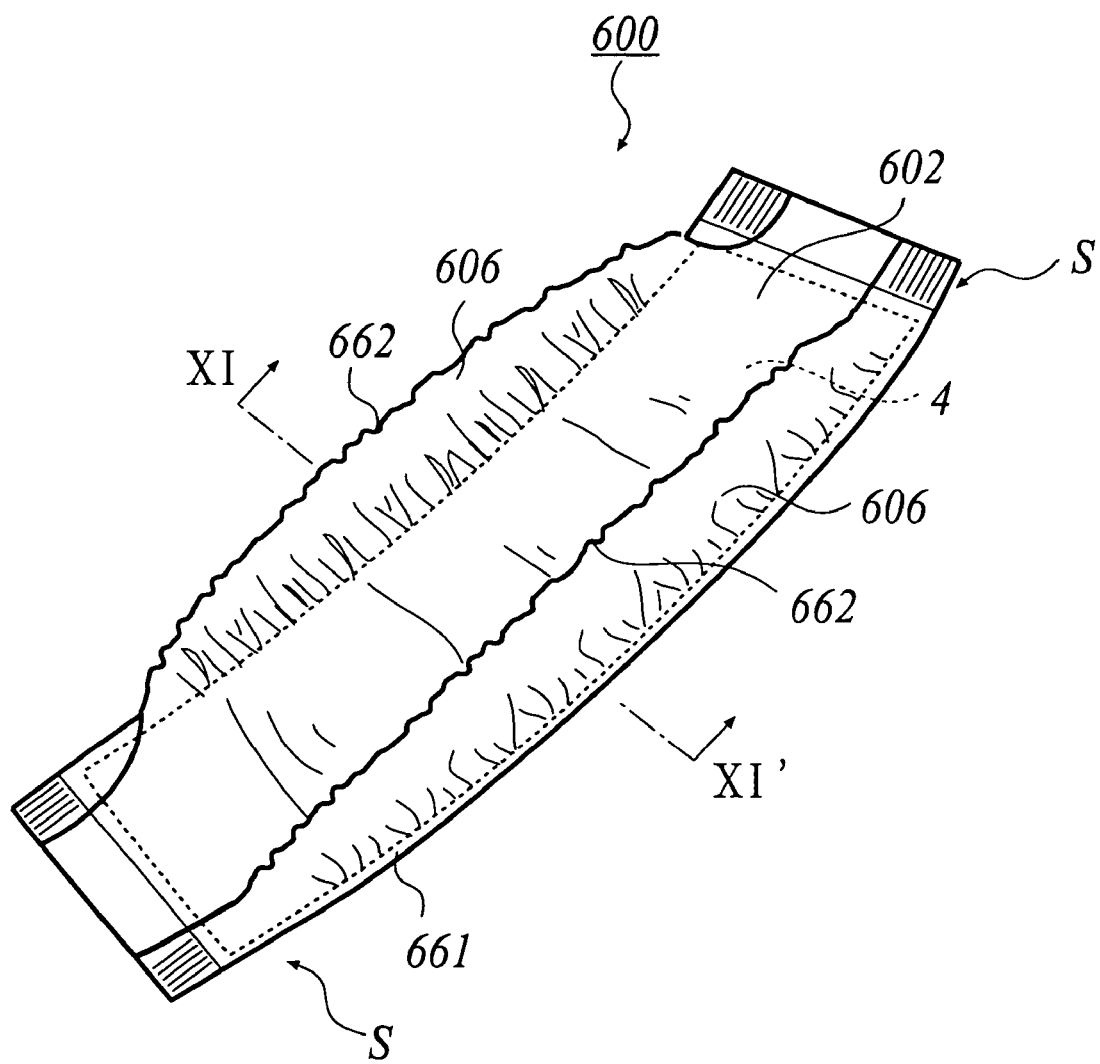
[FIG. 10] This is a perspective view illustrating an absorbent pad of Embodiment 7 using the absorbent article of the present invention.
Figure 11:
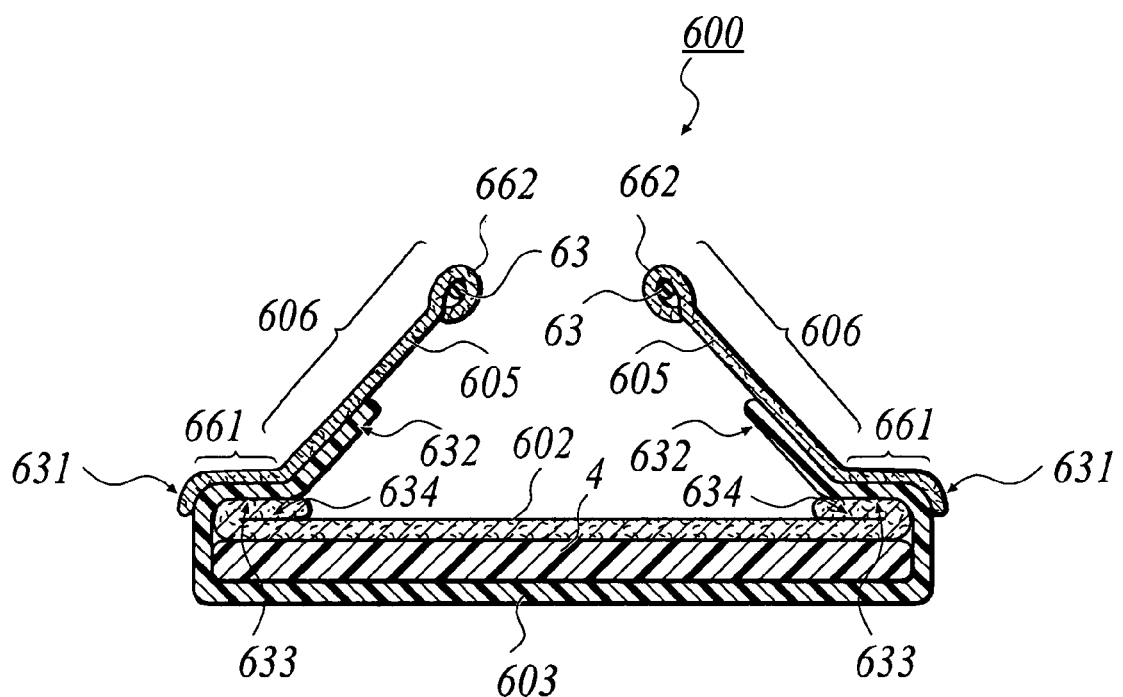
[FIG. 11] This is a cross-sectional view taken at XI-XI' of FIG. 10.

FIG. 10 is a perspective view illustrating the absorbent pad of Embodiment 7 using the absorbent article or the inner absorbent article of the present invention. FIG. 11 is a cross-sectional view taken at XI-XI' of FIG. 10.

As shown in FIGS. 10 and 11, the absorbent pad 600 is composed of, for example, a liquid-permeable topsheet 602 provided at a contacting face that contacts with a human body; a non liquid-permeable backsheet 603 that is positioned at a surface opposite to the topsheet 602 and is provided at an outer side when worn by a user; and the absorbent body 4 provided between the topsheet 602 and the backsheet 603.

The topsheet 602 is made of a liquid-permeable nonwoven fabric shaped to cover the surface side of the absorbent body (surface having a contact with a skin).

The topsheet 602 may be composed of nonwoven fabric including, for example, a plurality of preferable materials listed for the topsheet 2. Such a nonwoven fabric can be manufactured, for example, by a method similar to that for manufacturing the topsheet 2.

The backsheet 603 can be made with the same material as that of the backsheet 3. On a surface of the backsheet 603 that contacts with an underwear, an adhesive layer (not shown) is formed so that the absorbent pad 600 can be fixed to prevent the absorbent pad 600 from being dislocated from an underwear, a diaper, or a diaper external member (not shown) when used.

The backsheet 603 covers the bottom face of the absorbent body and also covers the side faces of the absorbent body 4. The backsheet 603 is folded up, to the topsheet 602, at both side portions in the longitudinal direction of the upper face of the absorbent body 4 from the folding starting point 631 as a starting point, thereby providing folding portions 632. Attachment portions 633 are provided at surfaces of both side portions in the longitudinal direction of the topsheet 602 that contacts with the absorbent body 4. The attachment portions 633 are adhered to a part of the folding portions 632. By folding the attachment portions 633 to the topsheet 602 and adhering the attachment portions 633 to the topsheet 602, the adhesion portions 634 are formed.

The attachment portion 633 and the adhesion portion 634 are adhered to each other by hotmelt adhesive and the like.

The absorbent body 4 is structured, for example, by covering an absorbent body core (not shown) with a liquid-permeable crepe paper (not shown). The absorbent body core is formed by combining an absorbent material such as cotton, pulp, or the like, and a sheet-like base such as fiber, film, or the like, with a superabsorbent resin such as superabsorbent polymer. The absorbent body core may have a single layer structure or may have a structure having a plurality of layers.

Next, three-dimensional gathers 606, 606 will be described. The three-dimensional gather 606 is structured to include: a folding portion 632 of the backsheet 603; and the gather sheet 605 made of a non liquid-permeable nonwoven fabric adhered to this folding portion 632. In particular, the three-dimensional gather 606 is provided, as shown in FIG. 11, by being adhered to a surface opposite to a surface of the folding portion 632 that face the topsheet 602, from the folding starting point 631 to the end portion of the folding portion 632.

The three-dimensional gather 606 also includes an elastic member 63 in the longitudinal direction so that the three-dimensional gather 606 is formed elastically in the longitudinal direction.

The three-dimensional gather 606 has a rising edge 661 that is positioned at the inner side in the width direction than the folding starting point 631 of the backsheet 603. The rising edge 661 is a root portion of the three-dimensional gather and is formed by adhering the attachment section 633 to the topsheet 602. Thus, the rising edge 661 is securely fixed to the topsheet 602 and can follow the movement of the absorbent pad 600.

On the other hand, since the gather sheet 605 protrudes from the folding portion 632, the vicinity of the free end 662 of the three-dimensional gather 606 is composed of only one layer of the gather sheet 605.

In other words, the rising edge 661 as a root portion of the three-dimensional gather 606 is composed of the topsheet 602, the backsheet 603, and the gather sheet 605. The vicinity of the free end 662 of the three-dimensional gather 606 which is a portion having a contact with skin (and being rubbed with skin in particular) is composed of only the gather sheet 605.

Furthermore, as shown in FIG. 10, although the three-dimensional gathers 606 are provided substantially along both side portions in the longitudinal direction of the absorbent body 4 without fixing the free ends 662, the three-dimensional gathers 606 are provided at both end portions S, S in the longitudinal direction of the absorbent pad 600 so that the free ends 662 of the three-dimensional gathers 606 are directly fold up to the topsheet 602 and are fixed to the topsheet 602.

The gather sheet 605 is made of a water-repellant nonwoven fabric.

As for adhesive used to adhere the gather sheet 605 to the backsheet 603, adhesive may be appropriately selected from, for example, ethylene-vinyl acetate copolymer resin (EVA; Ethylene Vinyl Acetate), polyvinyl alcohol (PVA), acrylamide polyvinyl alcohol copolymer, acrylic acid ester, vinyl acetate copolymer, carboxymethyl cellulose sodium, styrene-based elastomer (e.g., SIS, SBS, SIBS, SEPS), polyester acrylic elastomer, or polyolefin-based elastomer.

Adhesive may be coated, for example, by well-known methods such as curtain method, beat method, slot method, or spiral method (e.g., spray coating, blade coating).

According to the absorbent pad 600 of Embodiment 7 as described above, the attachment portion 633 formed by the folding portion 632 and the topsheet 602 is adhered to the topsheet 602 to provide the adhesion portion 634. As a result, the rising edge 661 as a root portion of the three-dimensional gather 606 is securely fixed to the topsheet 602. Thus, the three-dimensional gather 606 can be firmly raised with a sufficient height. This not only maintains the absorption performance but also provides a reliable appearance to a user.

In addition, since the root portion of the three-dimensional gather 606 is fixed, expansion in the lateral direction is prevented. Thus, the three-dimensional gather 606 can be prevented from protruding from a conveyor line and thus can be conveyed easily.

Furthermore, since the backsheet 603 covers the absorbent body 4 so as to cover from the bottom face of the absorbent body to side faces and a part of the upper face, the root portion of the three-dimensional gather 606 is structured, in a three-dimensional manner, by the backsheet 603 of a non liquid-permeable sheet. This can prevent body fluid pressed out of the absorbent body 4 from being leaked or oozed out from the root portion of the three-dimensional gather 606, when the absorbent pad 600 receives pressure from a user body.

Furthermore, since this structure has no side flap, the absorbent pad 600 is prevented from shrinking in the longitudinal direction. Thus, the absorbent pad 606 can be smoothly attached to an underwear, a diaper, or a diaper external member (not shown).

EMBODIMENT 8

Next, an absorbent pad 700 according to Embodiment 8 will be described with reference to FIG. 12.

Figure 12:
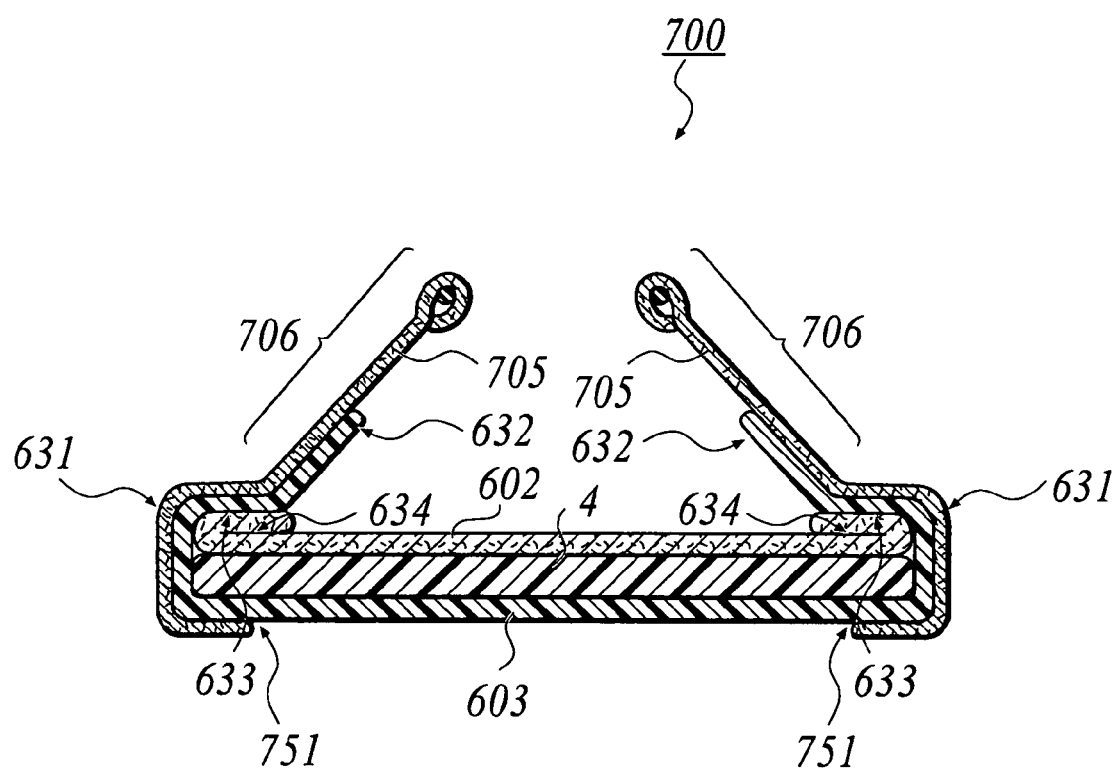
[FIG. 12] This is a cross-sectional view illustrating a part corresponding to XI-XI' of Embodiment 7 in an absorbent pad of Embodiment 8 using the absorbent article of the present invention.

FIG. 12 is a cross-sectional view illustrating the absorbent pad 700 of Embodiment 8 of the present invention.

The absorbent pad 700 shown in FIG. 12 is has a gather sheet 705 that is different from that of the absorbent pad 600 of Embodiment 7. Thus, Embodiment 8 will be described so that the same components as those of Embodiment 7 have the same reference numerals and will not be described further.

As shown in FIG. 12, the absorbent pad 700 has the backsheet 603 that covers the bottom face and side faces of the absorbent body 4 and is folded up to the topsheet 602 at both side portions in the longitudinal direction of the upper face of the absorbent body from the folding starting point 631 as a starting point, thereby providing the folding portion 632. The folding portions 632 are partially adhered to both side portions in the longitudinal direction of the topsheet 602 that contacts with the absorbent body 4 to provide the attachment portion 633. The attachment portions 633 are fold up to the topsheet 602 and are adhered to the topsheet 602, thereby providing the adhesion portions 634.

Furthermore, the gather sheets 705 forming the three-dimensional gathers 706, 706 of the absorbent pad 700 completely cover the folding portions 632 of the backsheet 603 to extend from side faces of the absorbent body 4 to bottom face of the absorbent body 4. The adhesion starting points 751 are adhered to the backsheet 603 so as to be positioned at bottom face of the absorbent body 4. In other words, the gather sheets 705 are adhered from the inner sides in the width direction of the folding starting points 631 of the folding portions 632 as the adhesion starting points 751. Thus, when compared with Embodiment 7, Embodiment 8 provides a very large area in which the gather sheets 705 are adhered to the backsheet 603 and thus the gather sheets 705 can be adhered in a sufficient area.

According to the absorbent pad 700 of Embodiment 8 as described above, the gather sheet 705 can be adhered to the backsheet 603 with a sufficient area. Thus, the leakage or oozing of body fluid can be prevented more effectively and the backsheet 603 can be completely prevented from contacting skin. This not only improves the sense of use but also reduces skin troubles.

EMBODIMENT 9

Next, an absorbent pad 800 according to Embodiment 9 will be described with reference to FIG. 13.

Figure 13:
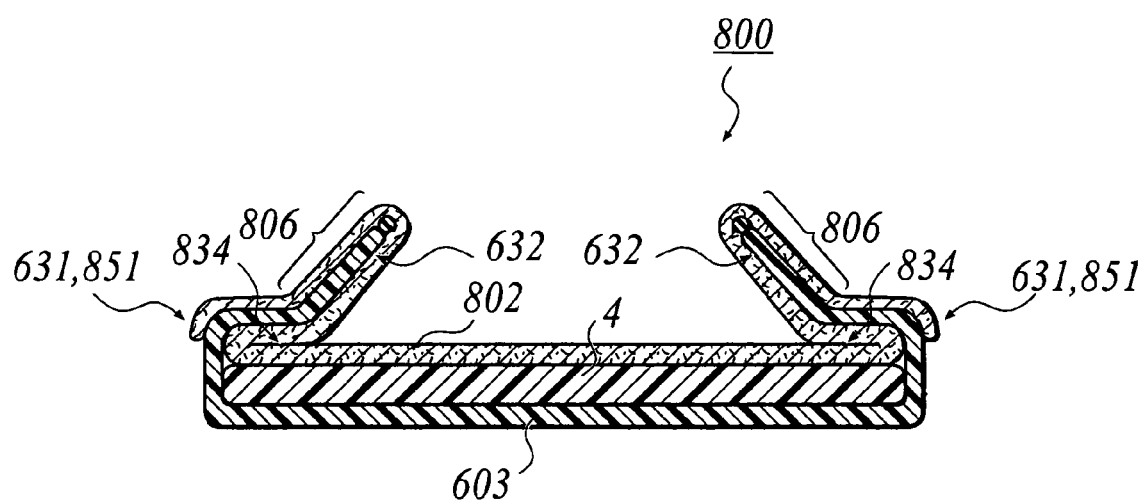
[FIG. 13] This is a-cross-sectional view illustrating a part corresponding to XI-XI' of Embodiment 7 in an absorbent pad of Embodiment 9 using the absorbent article of the present invention.

FIG. 13 is a cross-sectional view illustrating the absorbent pad 800 of Embodiment 9 of the present invention.

The absorbent pad 800 shown in FIG. 13 has a topsheet 802 different from that of the absorbent pad of Embodiment 7. Thus, Embodiment 9 will be described so that the same components as those of Embodiment 7 have the same reference numerals and will not be described further.

As shown in FIG. 13, the absorbent pad 800 has three-dimensional gathers 806, 806 composed of a topsheet 802 and the backsheet 603. The backsheet 603 covers the bottom face of the absorbent body and also covers side faces of the absorbent body 4. The backsheet 603 are folded up, to the topsheet 802, at both side portions in the longitudinal direction of upper faces of the absorbent body 4 from the folding starting points 631 as a starting point, thereby providing the folding portions 632.

On the other hand, both surfaces of the folding portion 632 of the backsheet 603 that are fold up to the topsheet 802 are entirely covered by the topsheet 802 and the folding starting point 631 becomes an adhesion starting point 851, thereby providing a three-dimensional gather 806.

Specifically, the three-dimensional gather 806 is composed of three layers of the backsheet 603 and the topsheets 802 sandwiching from the both surfaces of the backsheet 603.

Furthermore, in the vicinity of the folding starting point 631 constituting the root portion of the three-dimensional gather 806, the backsheet 603 that is entirely covered by the topsheet 802 is adhered to the topsheet 802. As a result, the adhesion portion 834 is provided to fix the root portion of the three-dimensional gather 806.

In the above structure, a region of the topsheet 802 covering the upper face of the absorbent body 4 (i.e., body fluid absorption region) is liquid-permeable and a region forming the three-dimensional gather 806 is not liquid-permeable. As for such liquid-permeable nonwoven fabric, the one that is included in the list of nonwoven fabrics in the description of the topsheet 2 can be used. As for such non liquid-permeable nonwoven fabric, the one that is included in the list of nonwoven fabrics in the description of the backsheet 603 can be used.

According to the absorbent pad 800 of Embodiment 9, the three-dimensional gather 806 is composed of the backsheet 603 and the topsheet 802 that cover both surfaces of the backsheet 603. This can prevent body fluid pressed out of the absorbent body 4 from oozing from the root portion of the three-dimensional gather 806 to outside, when the absorbent pad 800 receives a pressure from a user body.

Furthermore, since the folded backsheet 603 is covered by the topsheet 802, the folded backsheet 603 is prevented from contacting with human body and thus stimulation to skin can be reduced when the absorbent pad is worn by a user. This not only improves the sense of use but also reduces skin troubles.

In addition, the three-dimensional gather 806 is covered by the topsheet 802 made of a nonwoven fabric and therefore has clothlikeness, thus providing a soft sense of use to a user.

Furthermore, since the root portion of the three-dimensional gather 806 is adhered to the topsheet 802, the three-dimensional gather 806 is raised firmly with a sufficient height. This not only maintains the absorption performance but also provides a reliable appearance to a user.

Furthermore, since the root portion of the three-dimensional gather 806 is fixed, the three-dimensional gather 806 is suppressed from expanding in the width direction. Thus, the three-dimensional gather 806 can be prevented from protruding from a conveyor line and thus can be conveyed easily without causing the products to have variation in shape.

Furthermore, since the three-dimensional gather 806 is composed of the non liquid-permeable backsheet 603 and the topsheet 802, body fluid can be prevented more securely from oozing out.

EMBODIMENT 10

Next, an absorbent pad 900 according to Embodiment 10 will be described with reference to FIG. 14.

Figure 14:
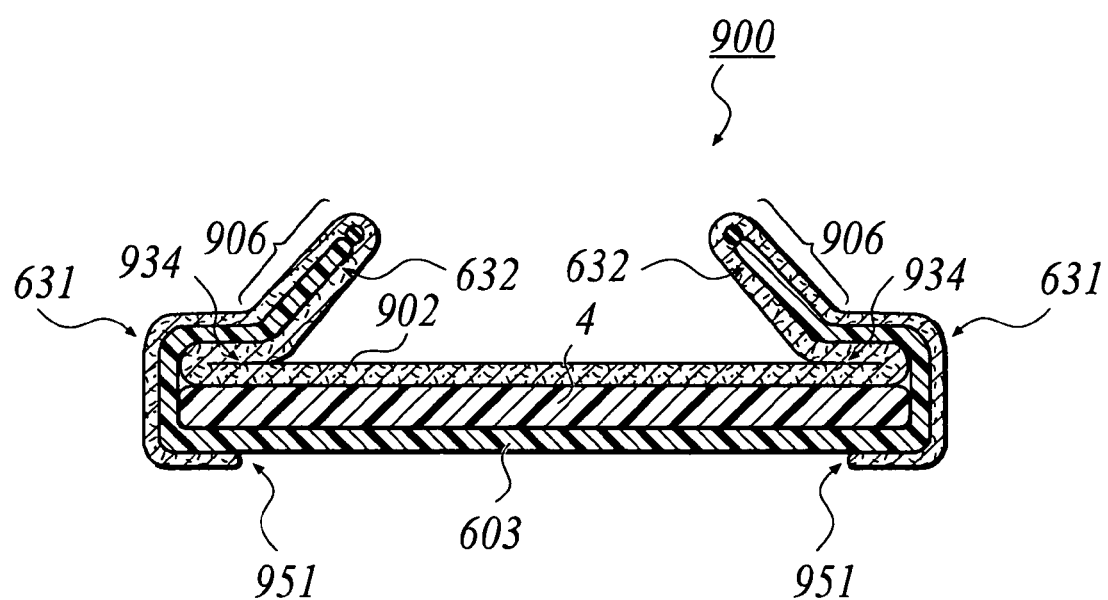
[FIG. 14] This is a cross-sectional view illustrating a part corresponding to XI-XI' of Embodiment 7 in an absorbent pad of Embodiment 10 using the absorbent article of the present invention.

FIG. 14 is a cross-sectional view illustrating the absorbent pad 900 of Embodiment 10 of the present invention.

The absorbent pad 900 shown in FIG. 14 has a topsheet 902 different from that of the absorbent pad of Embodiment 9. Thus, Embodiment 10 will be described so that the same components as those of Embodiment 9 have the same reference numerals and will not be described further.

As shown in FIG. 14, the absorbent pad 900 has three-dimensional gathers 906, 906 composed of a topsheet 902 and the backsheet 603. The backsheet 603 covers the bottom face of the absorbent body 4 and also covers side faces of the absorbent body 4. The backsheet 603 is folded up, to the topsheet 902, at both side portions in the longitudinal direction of the upper face of the absorbent body 4, from the folding starting point 631 as a starting point, thereby providing folding portions 632.

On the other hand, both surfaces of the folding portion 632 of the backsheet 603 that are fold up to the topsheet 902 are covered by the topsheet 902, and side faces of the absorbent body 4 are also covered by the topsheet 902. An adhesion starting point 951 is provided on the backsheet 603 that covers the bottom face of the absorbent body 4, thereby providing the three-dimensional gather 906.

In other words, the three-dimensional gather 906 is composed of three layers of the backsheet 603 and the topsheet 902 that sandwich the backsheet 603 and is adhered from the adhesion starting point 951 at an inner side in the width direction of the folding starting point 631.

Furthermore, concerning rising edge as a root portion of the three-dimensional gather 906, the backsheet 603 that is covered by the topsheet 902 is adhered to the topsheet 902 in the vicinity of the folding starting point 631 to provide an adhesion section 934, and thus the root portion of the three-dimensional gather 906 is fixed.

In the above structure, a region of the topsheet 902 covering the upper face of the absorbent body 4 (i.e., body fluid absorption region) is liquid-permeable and a region forming the three-dimensional gather 906 is not liquid-permeable. As for such liquid-permeable nonwoven fabric, the one that is included in the list of nonwoven fabrics as an example of the topsheet 2 can be used. As for such non liquid-permeable nonwoven fabric, the one that is included in the list of nonwoven fabrics as an example of the backsheet 3 can be used.

According to the absorbent pad 900 of Embodiment 10, an adhesion region of the topsheet 902 and the backsheet 603 that structure the three-dimensional gather 906 can be increased, thus leakage or oozing of body fluid can be prevented more effectively.

EMBODIMENT 11

Next, an absorbent pad 1000 according to Embodiment 11 will be described with reference to FIG. 15.

Figure 15:
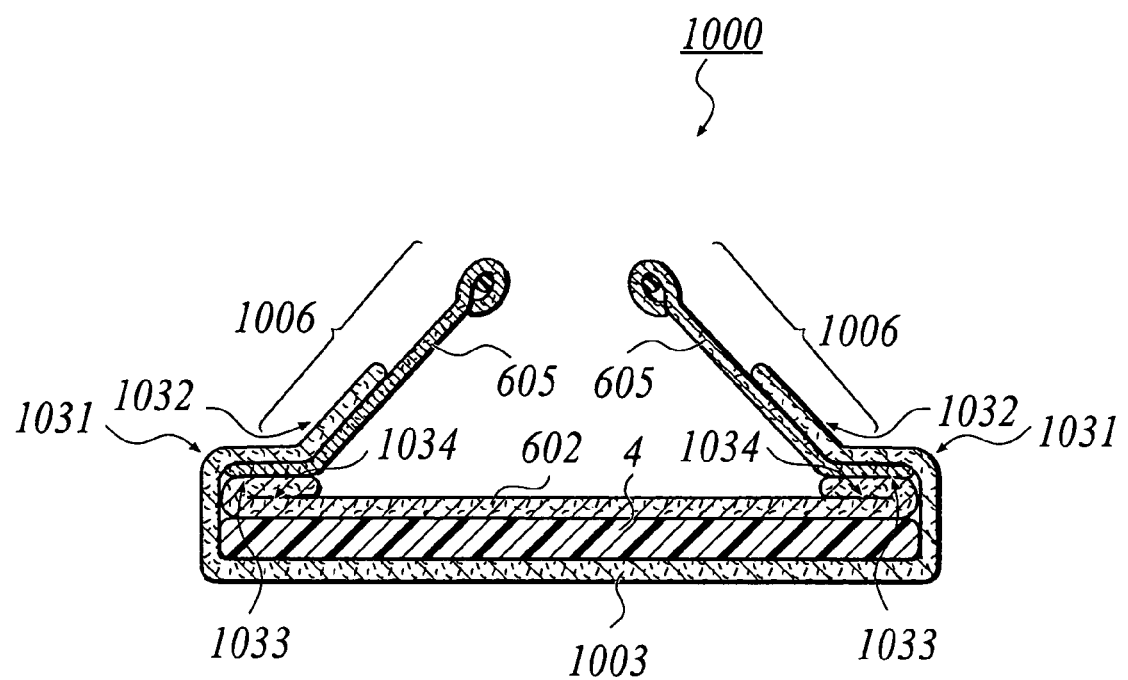
[FIG. 15] This is a cross-sectional view illustrating a part corresponding to XI-XI' of Embodiment 7 in an absorbent pad of Embodiment 11 using the absorbent article of the present invention.

FIG. 15 is a cross-sectional view illustrating the absorbent pad 1000 of Embodiment 11 of the present invention.

The absorbent pad 1000 shown in FIG. 15 has the topsheet 602 and the gather sheet 605 that have the same shapes as those of Embodiment 7 but has a different arrangement of the respective sheets for providing the three-dimensional gather 1006. Thus, Embodiment 11 will be described so that the same components as those of Embodiment 7 have the same reference numerals and will not be described further.

As shown in FIG. 15, the absorbent pad 1000 has three-dimensional gathers 1006, 1006 composed of a backsheet 1003 and the gather sheet 605. In this Embodiment, the gather sheet 605 is adhered to a surface of a folding portion 1032 of the backsheet 1003 that is folded up from the folding starting point 1031 as a starting point, that also face the topsheet 602. In particular, the gather sheet 605 is adhered to the backsheet 1003 from the folding starting point 1031 to the folding portion 1032 and is adhered to a surface of the topsheet 602 that contacts with the absorbent body 4, thereby providing an attachment portion 1033.

Furthermore, in the vicinity of a folding starting point 1031 that structure the root portion of the three-dimensional gather 1006, the attachment portion 1033 is adhered to the topsheet 602, thereby providing the adhesion portion 1034 to fix the root portion of the three-dimensional gather 1006.

In the above structure, the backsheet 1003 is composed of a ramie nonwoven fabric comprising a non liquid-permeable film layer and a breathable nonwoven fabric layer. In this structure, the non liquid-permeable film layer is provided on the absorbent body 4 side, while the breathable nonwoven fabric layer is positioned on the outside which is an opposite side of the non liquid-permeable film layer.

Here, the term "ramie nonwoven fabric" means, a nonwoven fabric called a laminate nonwoven fabric in which a nonwoven fabric is layered on a polyethylene sheet for example.

Next, an example of a method for manufacturing the absorbent pad 1000 will be described with reference to FIG. 16.

Figure 16:
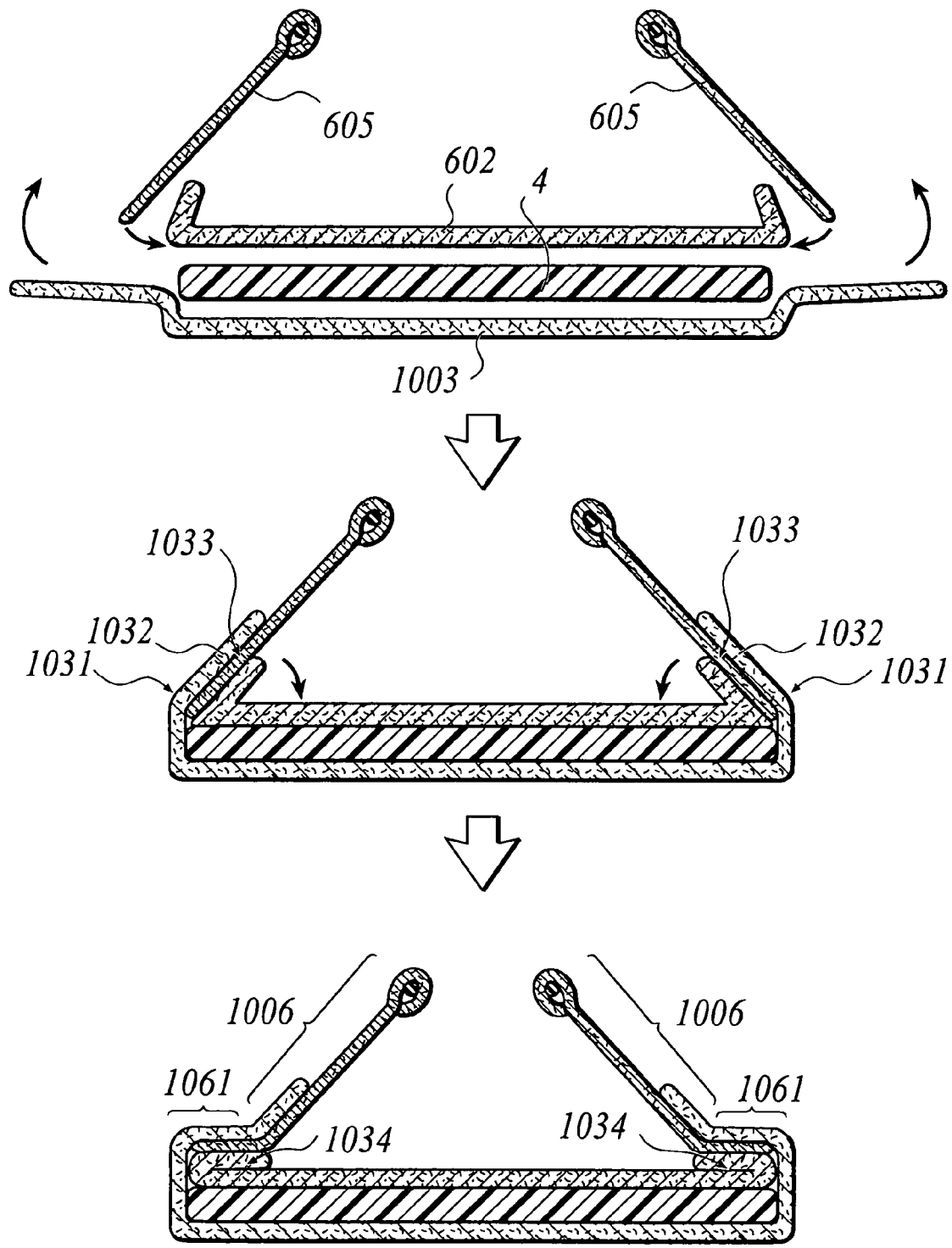
[FIG. 16] This illustrates a method for manufacturing the absorbent pad of FIG. 15.

FIG. 16 illustrates a method for manufacturing the absorbent pad 1000.

As shown in FIG. 16, the absorbent body 4 is placed on the upper face of the backsheet 1003, and the topsheet 602 is placed on its upper face. Further, the gather sheets 605 are provided on the upper face of the topsheet 602, where is also the upper face of the backsheet 1003 positioned in exterior to the left and right side portions in the longitudinal direction of the topsheet 602. Here, the topsheet 602 has a length in the lateral direction (width) that is shorter than the length of the backsheet 1003 in the lateral direction (width). Thus, the backsheet 1003 has a direct contact with the gather sheets 605 at both end portions in the width direction of the backsheet 1003 (i.e., both side portions in the longitudinal direction).

Next, the backsheet 1003 is folded up, to the topsheet 602, substantially along both side portions in the longitudinal direction of the absorbent body 4 from the folding starting point 1031 as a starting point to form the folding portions 1032. Then, both side portions in the longitudinal direction of the topsheet 602 are adhered to a part of the folding portion 1032 to form the attachment portions 1033. In this structure, the gather sheet 605 is sandwiched between the topsheet 602 and the backsheet 1003. That is, the attachment portion 1033 is composed of three layers, the topsheet 602, the gather sheet 605, and the backsheet 1003, from the inner side.

Next, the attachment portions 1033 are further fold up to the topsheet 602 to adhere the topsheets 602 to each other to provide the adhesion portions 1034. As a result, rising edges 1061 are formed as a root portion of the three-dimensional gathers 1006.

According to the absorbent pad 1000 of Embodiment 11 as described above, the backsheet 1003 has clothlikeness, thus a user can expect a soft sense of use.

EMBODIMENT 12

Next, an absorbent pad 1100 according to Embodiment 12 will be described with reference to FIG. 17 through FIG. 23.

Embodiment 12 will be described by, for example, an absorbent article directly attached to an underwear (such as sanitary napkin) or an inner absorbent article attached to a diaper or a diaper external member for use (such as urine absorption pad).

Figure 17:
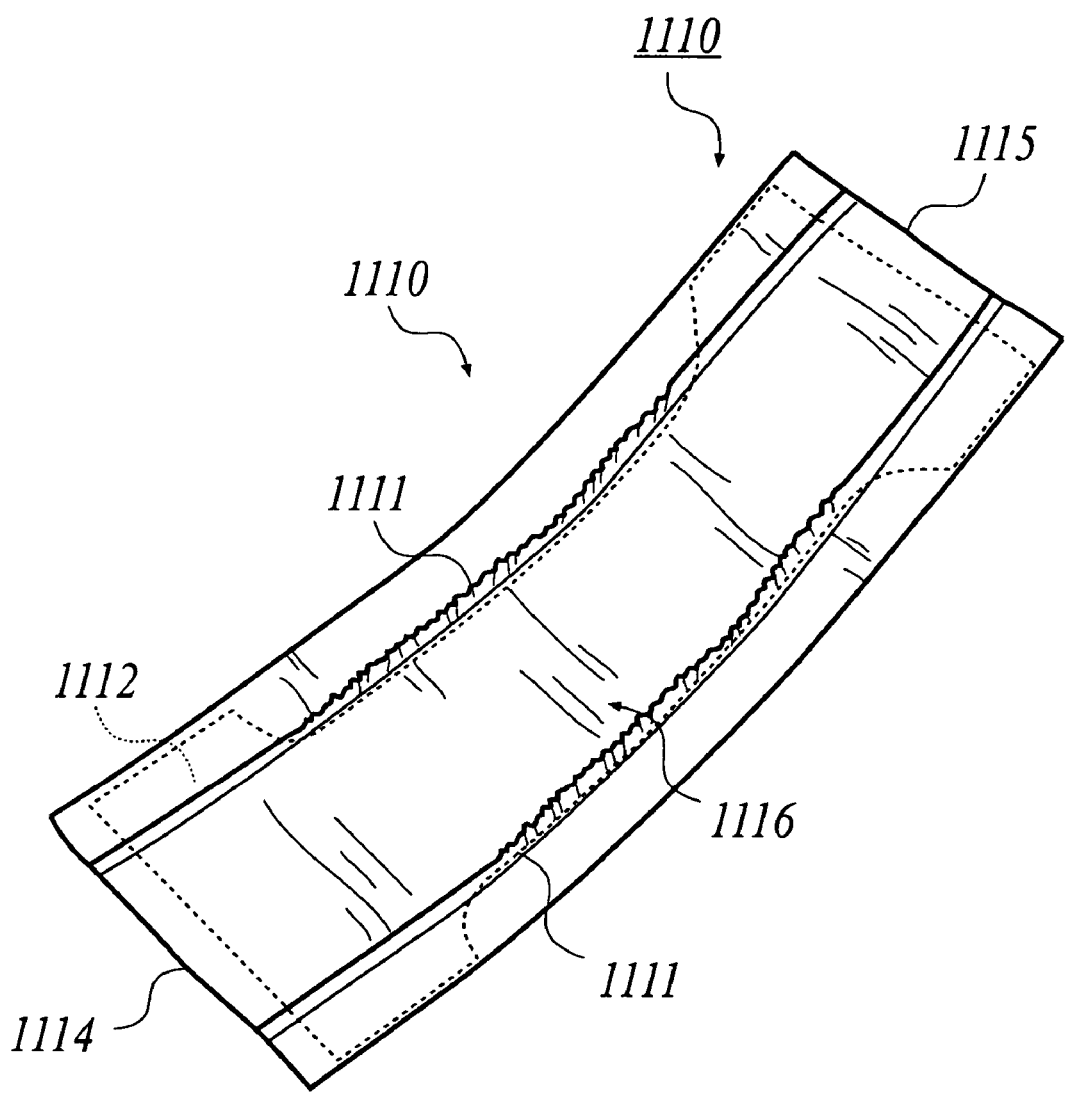
[FIG. 17] This is a perspective view illustrating an absorbent pad of Embodiment 12 using the absorbent article of the present invention.
Figure 18:
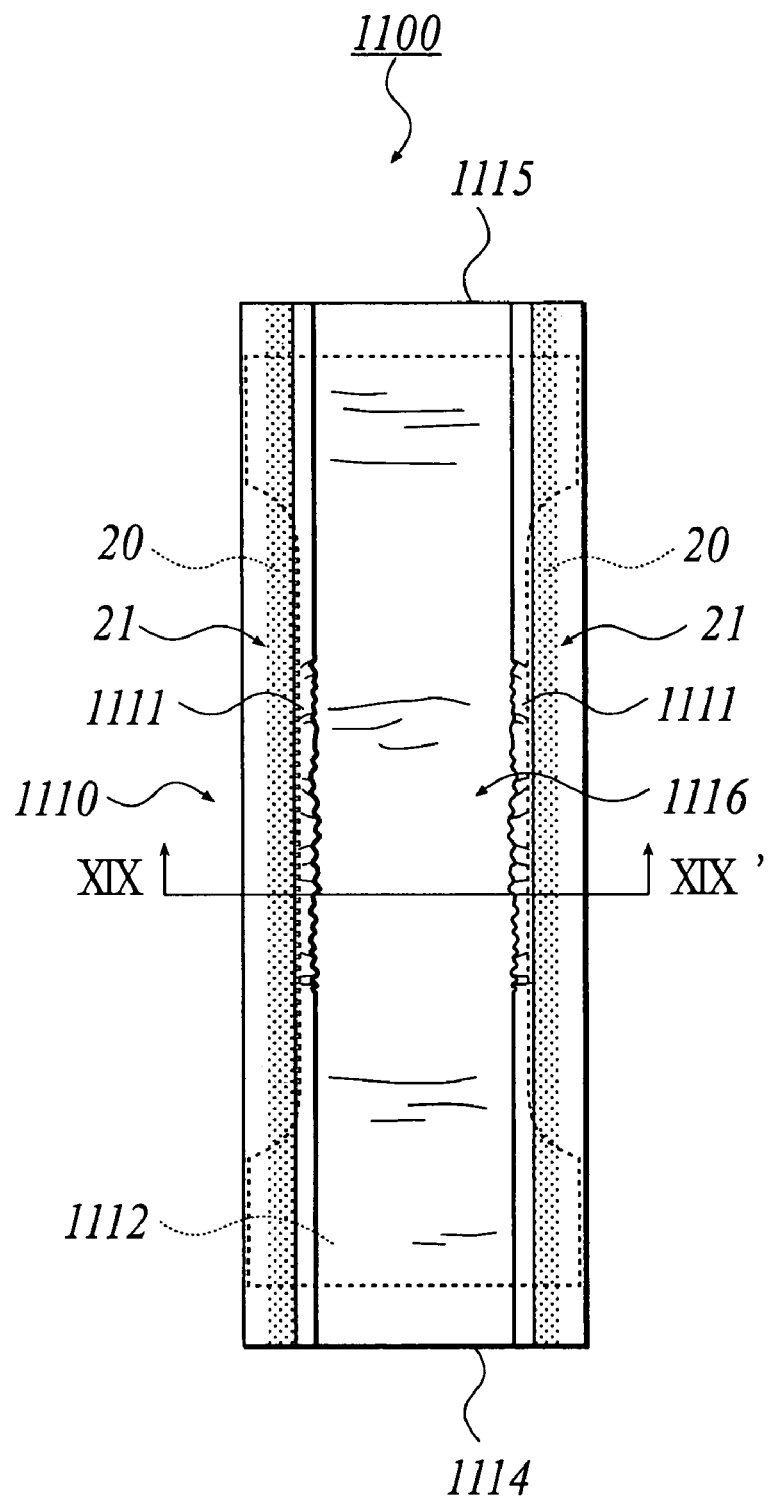
[FIG. 18] This is a top view of an absorbent pad of FIG. 18.
Figure 19:
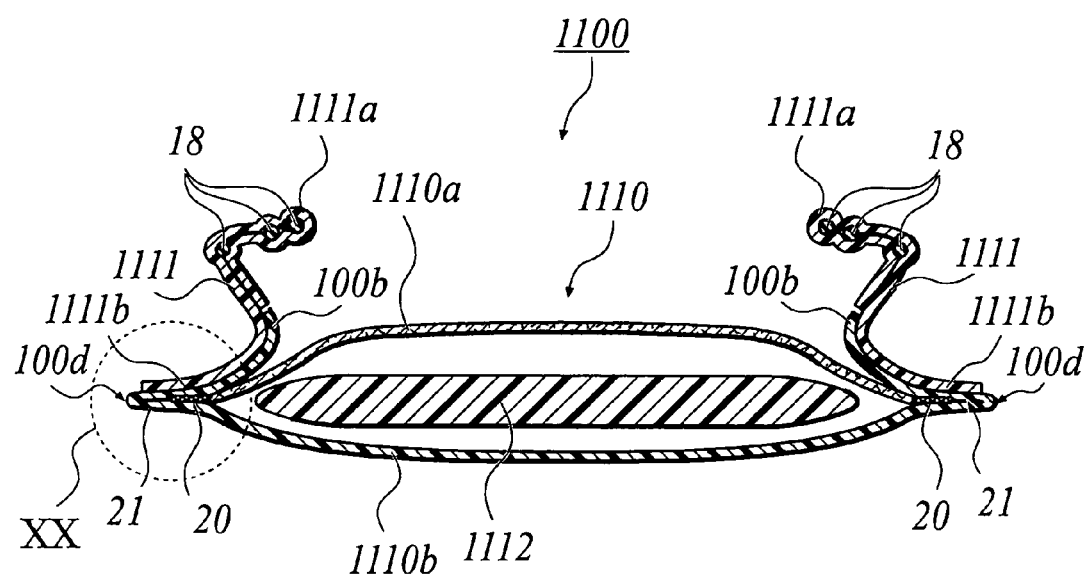
[FIG. 19] This is a cross-sectional view at XIX-XIX' of FIG. 18.

FIG. 17 is a perspective view of expanded absorbent pad 1100 of Embodiment 12. FIG. 18 is a plane view of the absorbent pad 1100. FIG. 19 is a cross-sectional view taken at XIX-XIX' of FIG. 18.

As shown in FIG. 17 through FIG. 19, the absorbent pad 1100 as an absorbent article is composed of an absorbent pad body 1110 and a pair of left and right gather sheets 1111, 1111 for example.

The absorbent pad body 1110 is provided at a surface that contacts with a human body and is composed of, for example: a liquid-permeable topsheet 1110a which permeates body fluid (e.g., urine) speedily; a non liquid-permeable backsheet 1110b provided at a surface opposite to the surface that contacts with a human body; and an absorbent body 1112 sandwiched by the backsheet 1110b and the topsheet 1110a.

This absorbent pad body 1110 also has a belly-side portion 1114 at one end portion thereof so that the absorbent pad body 1110 covers a crotch portion of a human body from a belly side to a back side. The other end portion thereof has a back-side portion 1115. The belly-side portion 1114 and the back-side portion 1115 have therebetween a crotch portion 1116.

The topsheet 1110a is made of a porous or nonporous nonwoven fabric, or of a porous plastic sheet for example. The topsheet 1110a can be made of a nonwoven fabric such as the one included in the list of a plurality of preferable materials for the topsheet 2. Such nonwoven fabric can be manufactured, for example, by the same manufacturing method as that of the topsheet 2.

When the topsheet 1110a is formed with a large number of permeation holes, body fluid can be absorbed more speedily, thus providing an excellent dry touch feeling.

The backsheet 1110b is formed with a sheet material having at least a water shielding characteristic, such as polyethylene. The backsheet 1110b can be formed with, for example, the same material as that of the backsheet 3.

As shown in FIG. 19, the end portions in the width direction of backsheet 1110b are folded up to the inner side of the backsheets 1110b to form a layered structure. The folding portion 100b where the backsheet 1110b is folded up is formed with an adhesive coating region that is coated with adhesive, and an adhesive non-coating region that is not coated with adhesive.

Specifically, the end portions in the width direction of the backsheet 1110b are folded up to the inner sides of the backsheet 1110b to sandwich the topsheet 1110a. The folding portion 100b where the backsheet 1110b is folded up is formed with the adhesive layer 20 including adhesive such as hotmelt, as an adhesive agent coating region, and adheres the folded layers of the backsheets 1110b to each another.

It is noted that the end portions in the width direction of the backsheet 1110b may also be folded up to the back face that is opposite to the topsheet 1110a.

In this structure, concerning the folding portion 100b of the backsheet 1110b, a stripe-shaped region including a folding portion 100d that is a folding starting point at which the backsheet 1110b is folded up, is formed with an adhesive non-coating region 21 without application of adhesive. Therefore, the backsheets 1110b are prevented from being adhered to each other at the folding portion 100d. That is, the adhesive non-coating region 21 is provided in the longitudinal direction of the backsheet 1110b so as to include the folding portion 100d that is a folding starting point.

It is noted that the adhesive layer 20 is provided, as shown in FIG. 18, from the belly-side portion 1114 of the absorbent pad body 1110 to the back-side portion 1115 so that the adhesive layer 20 is not provided at the folding portion 100d of the backsheet 1110b.

The absorbent body 1112 absorbs aqueous components such as urine as body fluid during the use of the absorbent pad 1100 and can be made of, for example, the same material as that of the absorbent body 4.

The absorbent body 1112 is formed to have a length ranging from the belly-side portion 1114 to the back-side portion 1115 of the of the absorbent pad body 1110. A center portion in the longitudinal direction of the absorbent body 1112 is formed to have a width narrower than the width of both end portions of the absorbent body 1112. That is, a portion corresponding to the crotch portion 1116 which is substantially center portion of the absorbent body 1112 has a width narrower than those of portions corresponding to the belly-side portion 1114 and the back-side portion 1115, that are the both end portions in the longitudinal direction of the absorbent body 1112, thereby providing a hourglass-like shape.

By providing a portion corresponding to the crotch portion 1116 that is substantially center portion of the absorbent body 1112 to have a width narrower than those of both end portions in the longitudinal direction as described above, the absorbent pad 1100 (absorbent pad body 1110) can be worn by a human body so that the absorbent body 1112 fits with the human body at the crotch section (inguina section) of the human body.

The gather sheets 1111, 1111 are provided to the backsheet 1110b that is folded up to the topsheet 1110a side of the absorbent pad body 1110, so as to extend from the belly-side portion 1114 to the back-side portion 1115. The gather sheets 1111, 1111 are provided by double-folding a non liquid-permeable sheet, and fixing the folded surfaces, by hotmelt, heat seal, and the like. In this gather sheet 1111, an end portion of the folding portion of the double-folded non liquid-permeable sheet is a free end portion 1111a and an end portion fixed to the backsheet 1110b is a fixed end portion 1111b.

This free end portion 1111a of the gather sheet 1111 has, along the longitudinal direction of the gather sheet 1111, a plurality of elastic members 18 such as string rubber, polyurethane fiber, and the like, arranged to be substantially parallel to each other. Within the gather sheets 1111, 1111 being fixed to the absorbent pad body 1110, the free end portions 1111a are raised from the absorbent pad body 1110, thus providing the three-dimensional gather. Within this structure, the elastic member 18 allows the three-dimensional gather to elastically change form so as to fit to the body of a user, thus providing a structure that easily fit the user.

It is noted that the fixed end portion 1111b of the gather sheet 1111 is fixed to a surface that is opposite to the topsheet 1110a at the folding portion 100b at which the backsheet 1110b is folded up.

In this manner, the gather sheets 1111, 1111 raised to the surface side of the topsheet 1110a are provided at edge portions in the width direction of the absorbent pad body 1110. Thus, emitted body fluid that is not absorbed by the absorbent body 1112 through the topsheet 1110a and flowed to edge portions in the width direction of the absorbent pad body 1110, is once stopped by the gather sheets 1111. Then, the flow of the body fluid is dispersed in the longitudinal direction and is absorbed by the absorbent body 1112, thereby providing an effect to prevent the lateral leakage of the body fluid.

In particular, the gather sheet 1111 is provided so that the backsheet 1110b is fixed to the folding portion 100b folded up to the topsheet 1110a. Thus, the gather sheet 1111 and the backsheet 1110b can block body fluid, and prevent the lateral leakage of body fluid more effectively.

Next, concerning the backsheet 1110b of the absorbent pad 1100, the adhesive agent non-coating region 21 and the adhesive layer 20 are provided so that the adhesive layer 20 is not provided at the folding portion 100d at which the backsheet 1110b is folded up. The adhesive layer 20 adheres portions where folded folding portion 100b of the backsheet 1110b are layered, with one another. Thus, the backsheets 1110b are prevented from being adhered to each other at the end portion of the folding portion 100d. The effect obtained from this will be described.

When the absorbent pad 1100 is worn by a human body for use, end portions in the width direction of the crotch portion 1116 of the absorbent pad 1100 contacts with the inguina portions of the human body (groins).

Figure 20A:
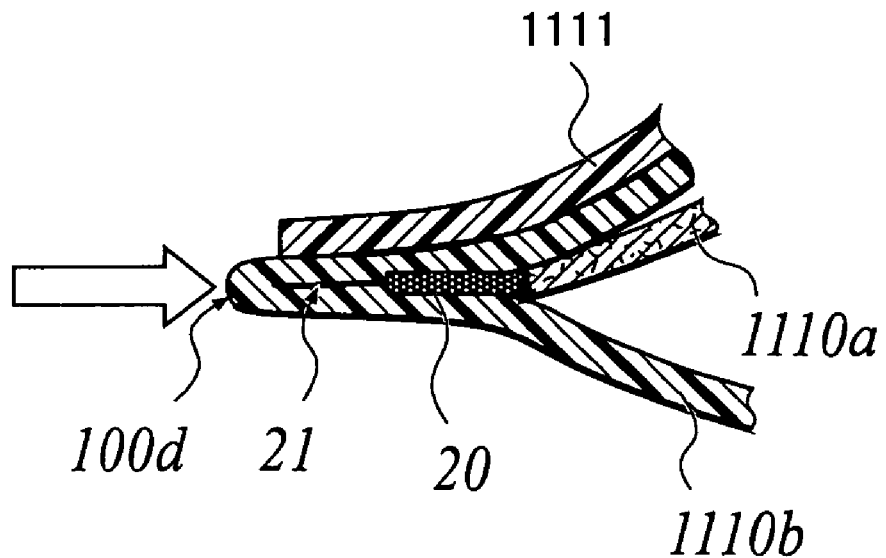
[FIG. 20A] This is an enlarged view illustrating a part XX of FIG. 19.
Figure 20B:
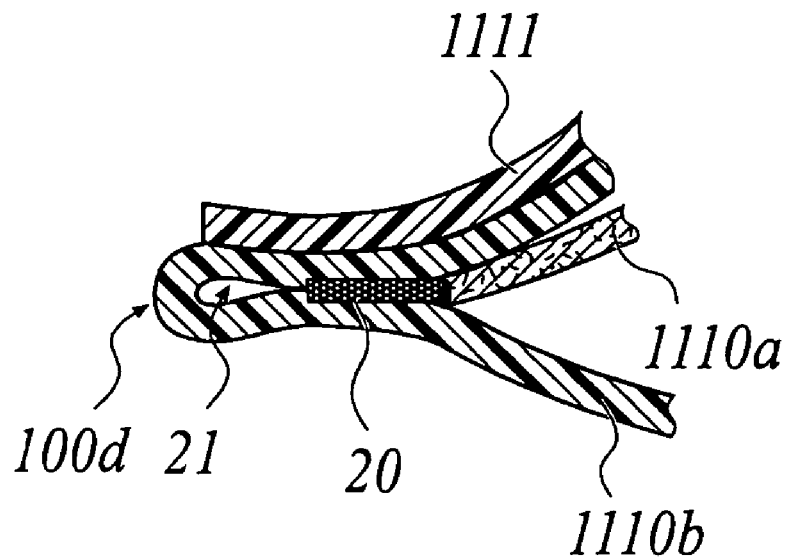
[FIG. 20B] This illustrates the deformation of the part XX of FIG. 19.

At this time, as shown in FIG. 20A, the folding portion 100d of the folding portion at which the backsheet 1110b is folded up receives a force in the direction as shown by the arrow.

When the folding portion 100d receives the force as described above, the folding portion 100d as shown in FIG. 20B at which the backsheets 1110b are not adhered to each other expands to form a loop-like shape in the cross sectional view. As a result, in the crotch portion 1116 of the absorbent pad 1100, the folding portion 100d as an end portion that contacts with a human body is rounded to increase the contact area with a human body. That is, the folding portion 100d (backsheet 1110b) having the loop-like shape in the cross sectional view is elastically deforms so as to provide a soft contact with a human body.

As described above, when the absorbent pad 1100 is worn by a human body, the end portion (folding portion 100d) at the crotch portion 1116 of the absorbent pad 1100 contacts with a human body is elastically deformed to have a loop-like shape in the cross sectional view, thus provides a soft contact with a human body. Therefore, the absorbent pad 1100 having the folding portion 100d as described above can be an absorbent pad comfortably worn by a user.

In particular, a portion corresponding to the crotch portion 1116 of the absorbent body 1112 of the absorbent pad 1100 has a width that is narrower than those of both end portions in the longitudinal direction, thus providing a shape that easily fit the crotch portion (inguina portion) of a human body. Thus, the absorbent pad 1100 can be comfortably worn by a user in a more preferable manner.

It is noted that the method for arranging adhesive so that the folding portion 100d as an end portion that contacts with a human body at the crotch portion 1116 of the absorbent pad 1100 is elastically deformed to have a loop-like shape in the cross sectional view is not limited to the one as shown in FIG. 18. That is, adhesive may not be provided at a portion of the folding portion 100d, at which the backsheet 1110b is folded up, that corresponds to a portion at which the absorbent body 1112 has a reduced width.

Figure 21:
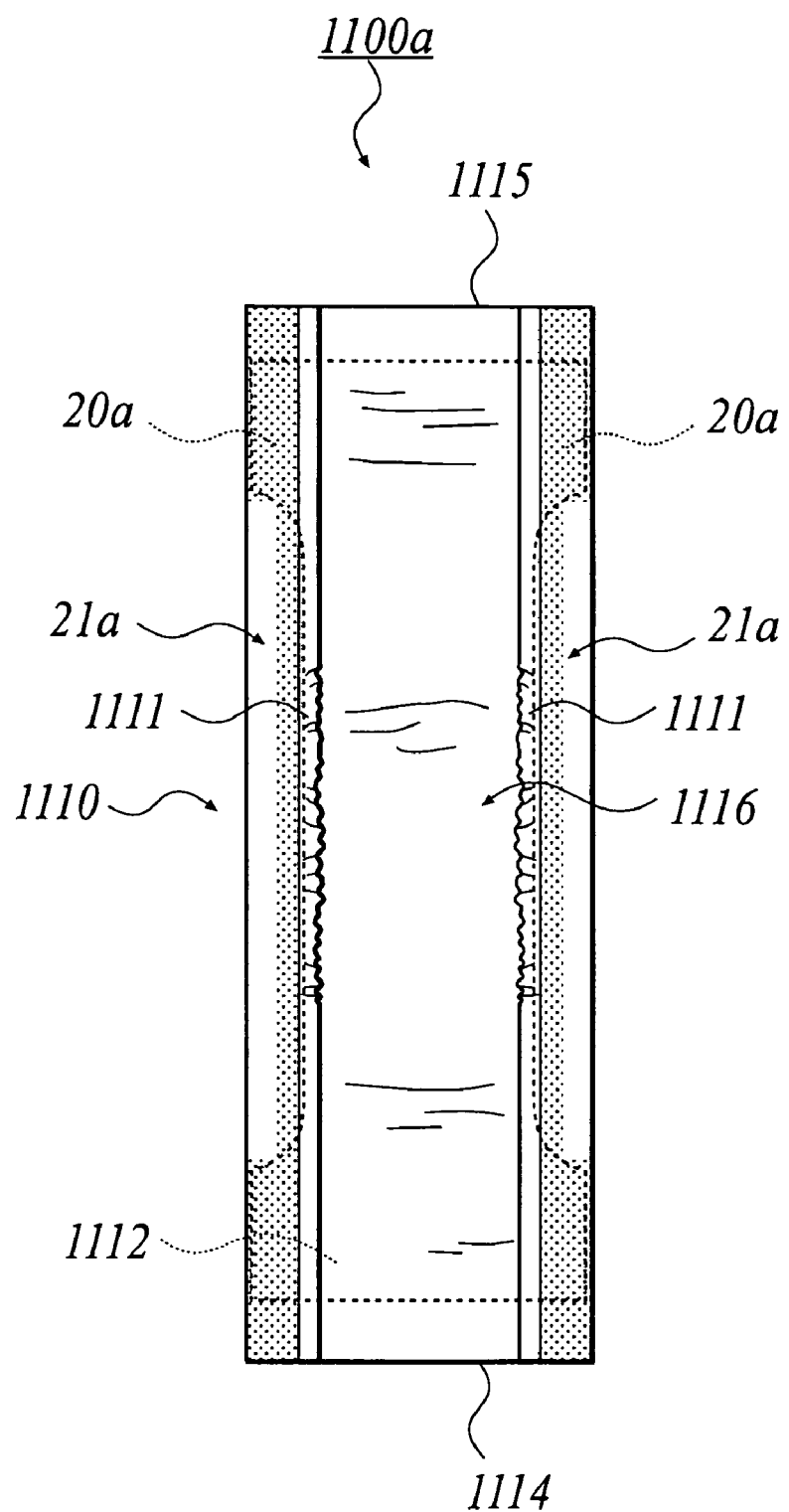
[FIG. 21] This is a top view illustrating a modification of an absorbent pad of Embodiment 12 using the absorbent article of the present invention.

For example, as shown in FIG. 21, the adhesive non-coating region 21 may be provided at least at a position corresponding to a portion that have a reduced width of the absorbent body 1112, that also includes the folding portion 100d as a folding starting point of the folding portion 100b. Specifically, to the portion of the absorbent pad 1100a at which end portions in the width direction of the backsheet 1110b are folded up to provide a layered structure (folding portions 100b), adhesive to adhere the backsheets 1110b to each other is provided over the entire surfaces of the folded parts of the backsheet 1110b. In the positions corresponding to the belly-side portion 1114 and the back-side portion 1115 of the absorbent pad body 1110, adhesive layers 20a as an adhesive coating region is provided over the entire surface of layered backsheet 1110b, and adhesive layers 20a is not provided on the folding portion 100d of the backsheet 1110b that is a position corresponding to the crotch portion 1116 at which the absorbent body 1112 has a reduced width. Thus adhesive layers 20a as an adhesive coating region and an adhesive non-coating regions 21a are provided from the belly-side portion 1114 to the back-side portion 1115 along a straight line.

Figure 22:
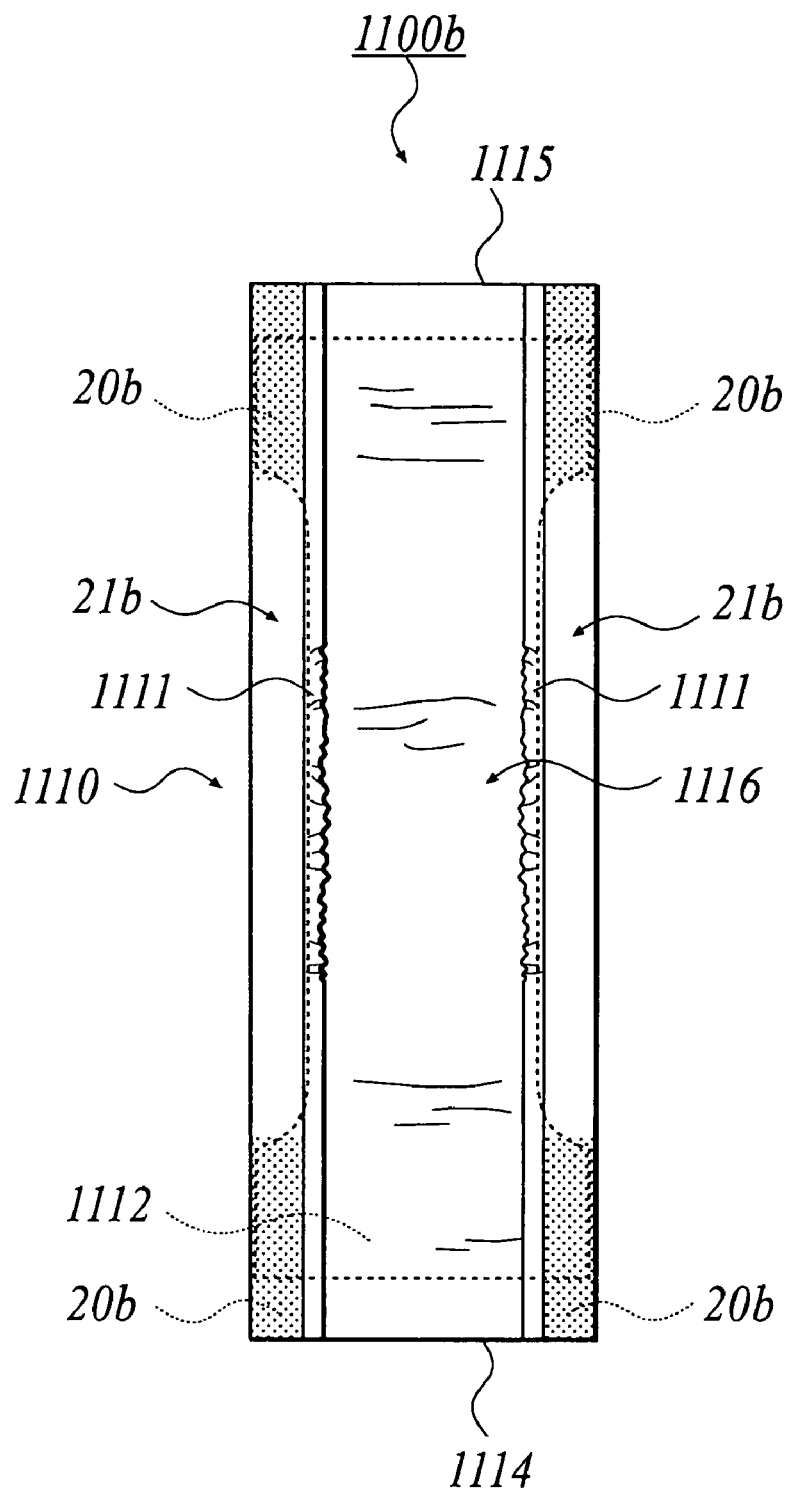
[FIG. 22] This is a top view illustrating a modification of an absorbent pad of Embodiment 12 using the absorbent article of the present invention.

Alternatively, as shown in FIG. 22, the adhesive non-coating region 21b may also be provided at a position corresponding to a portion at which the absorbent body 1112 has a reduced width, from the folding portion 100d as a folding starting point to the absorbent body 1112. Specifically, to the portion of the absorbent pad 1100a at which end portions in the width direction of the backsheet 1110b are folded up to provide a layered structure (folding portions 100b), adhesive to adhere the backsheets 1110b to each other is provided over the entire surfaces of the folded parts of the backsheet 1110b. Only in the positions corresponding to the belly-side portion 1114 and the back-side portion 1115 of the absorbent pad body 1110, adhesive layers 20b as an adhesive coating region is provided over the entire surface of layered backsheet 1110b. Thus adhesive layers 20b as an adhesive coating region and an adhesive non-coating regions 21b are provided.

Figure 23:
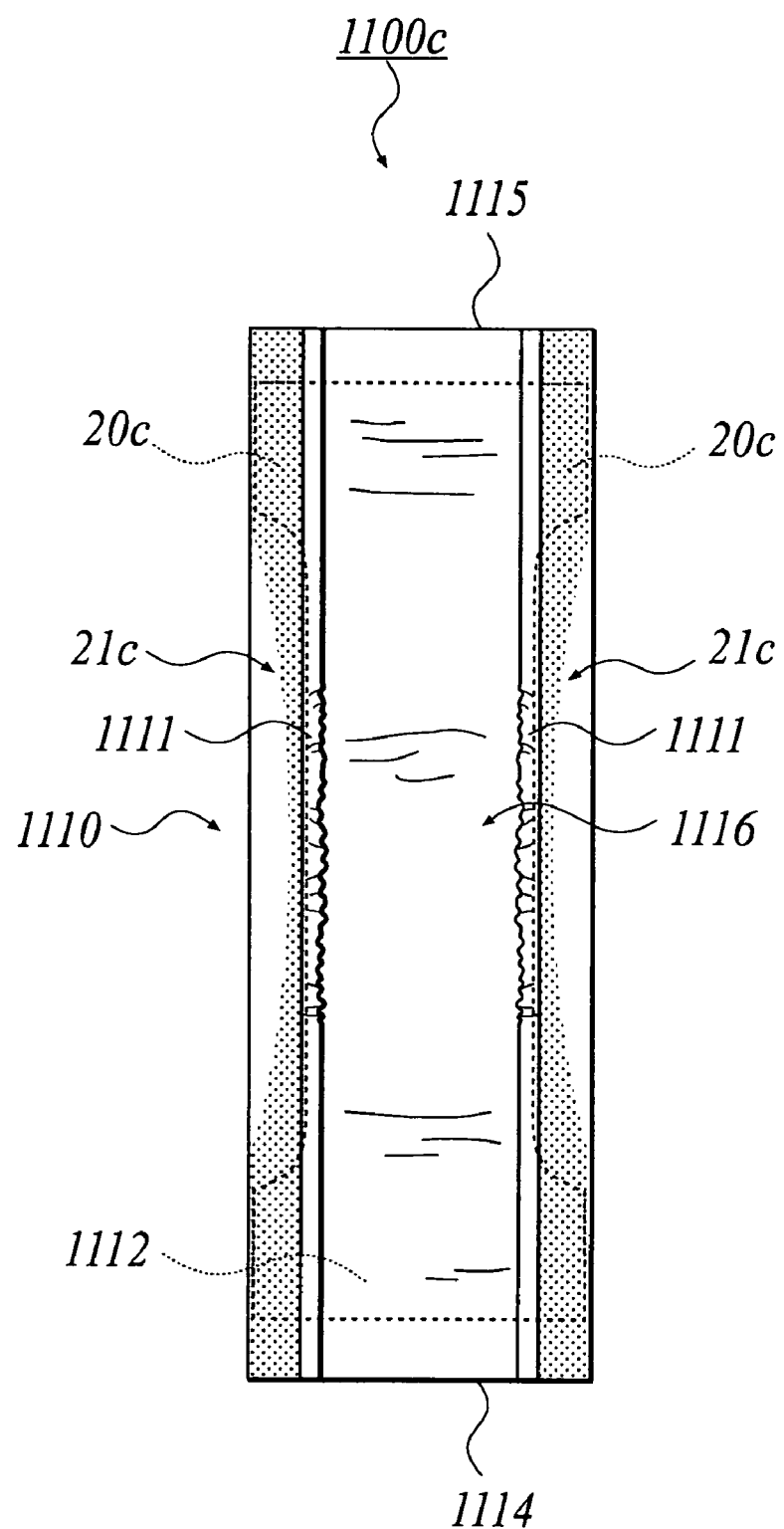
[FIG. 23] This is a top view illustrating a modification of an absorbent pad of Embodiment 12 using the absorbent article of the present invention.

Another arrangement as shown in FIG. 23 may also be used, wherein the adhesive non-coating region 21c is provided at a position of the absorbent body 1112 corresponding to a part having a reduced width, from the folding portion 100d as a folding starting point to the front of the absorbent body 1112. Specifically, to the portion of the absorbent pad 1100c at which end portions in the width direction of the backsheet 1110b are folded up to provide a layered structure (folding portions 100b), adhesive to adhere the backsheets 1110b to each other is provided over the entire surfaces of the folded parts of the backsheet 1110b. In the positions corresponding to the belly-side portion 1114 and the back-side portion 1115 of the absorbent pad body 1110, adhesive layers 20c as an adhesive coating region is provided over the entire surface of layered backsheet 1110b, and adhesive layers 20c is not provided on the folding portion 100d of the backsheet 1110b that is a position corresponding to the crotch portion 1116 at which the absorbent body 1112 has a reduced width. Thus adhesive layers 20c as an adhesive coating region and an adhesive non-coating regions 21c are provided from the belly-side portion 1114 to the back-side portion 1115 to have a shape inwardly curved from the folding portion 100d.

It is noted that, although the above-described embodiments have described the present invention with examples of, an absorbent pad that can be used as an absorbent article directly attached to an underwear (e.g., sanitary napkin) or as an inner absorbent article used to a diaper or a diaper external member (e.g., urine absorption pad), the present invention is not limited to these. The present invention can be preferably used, for a disposable paper diaper as an absorbent article that can be directly used, for example.

Figure 24:
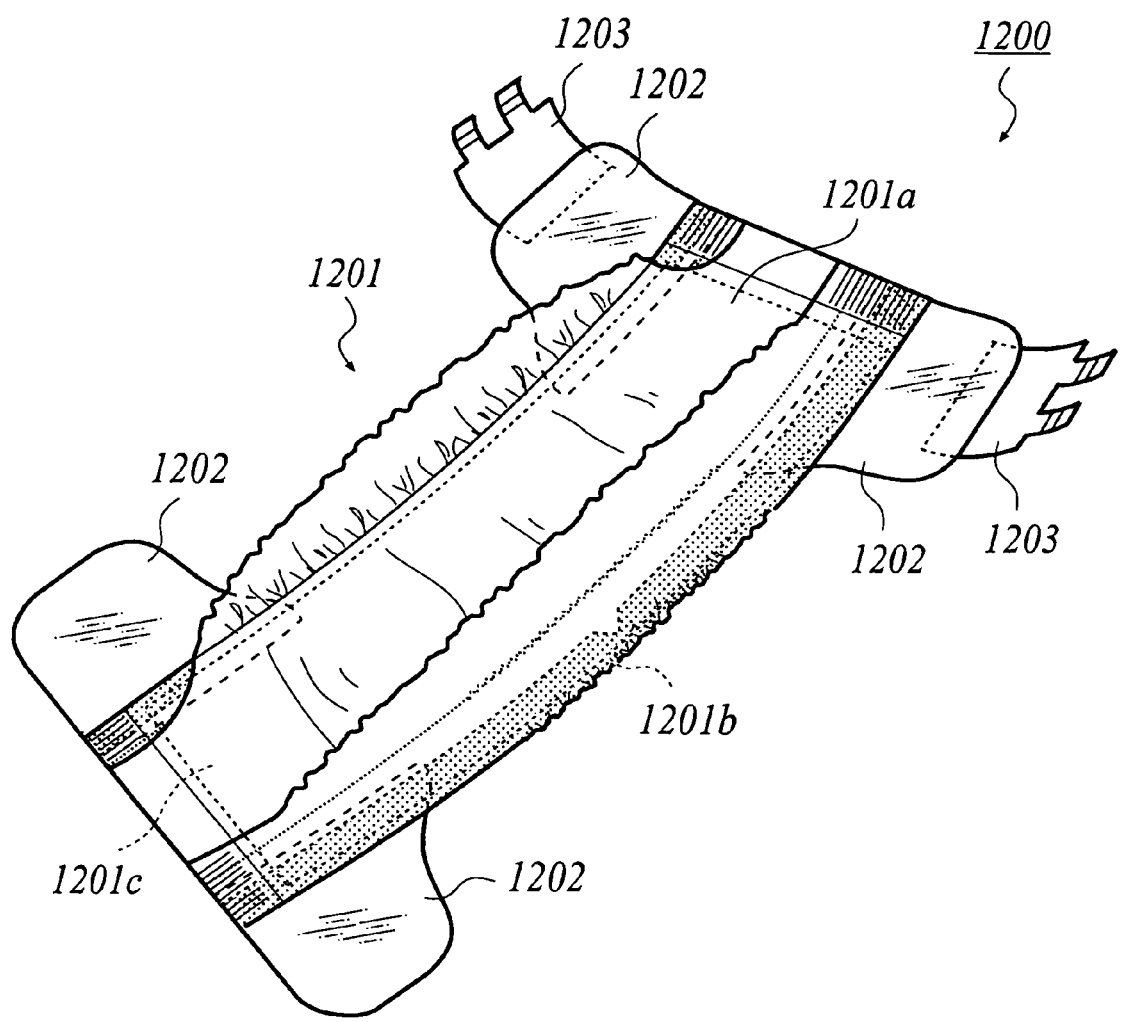
[FIG. 24] This is a development view of a disposable paper diaper using the absorbent article of the present invention.

Specifically, all of the Embodiments 1 through 12 can also be applied, for example, to absorbent articles such as a diaper 1200 as shown in a structure of FIG. 24. In this structure, a diaper body 1201 is structured to include: a liquid-permeable topsheet 1201a positioned at a surface that contacts with a human body; a non liquid-permeable backsheet 1201b positioned at a surface opposite to the topsheet 1201a; and an absorbent body 1201c provided between the topsheet 1201a and the backsheet 1201b. The diaper body 1201 is provided with: waist portions 1202 for retaining the diaper body 1201 around the waist of a user; fixing portions 1203 that are provided at the waist portions 1202 and fix the waist portions 1202 to each other, and the like.

INDUSTRIAL APPLICABILITY

The present invention can be used in a field of manufacturing absorbent articles.

DESCRIPTION OF REFERENCE NUMERALS 1, 100, 200, 300, 400, 500, 500a, 600, 700, 800, 900, 1000, 1100, 1100a, 1100b, and 1100c: Absorbent pad (absorbent article, inner absorbent article)
2, 202, 302, 502, 602, 802, 902, and 1110a: Top sheet
3, 403, 503, 603, 1003, and 1110b: Back sheet 4, 504, and 1112: Absorbent body
5, 105, 505, 605, 705, and 1111: Gather sheet
6, 106, 206, 306, 406, 506, 606, 706, 806, 906, and 1006: Three-dimensional gather
31, 431, 531, 631, 1031, and 100d: Folding starting point
32, 432, 532, 632, 1032, and 100b: Folding portion
51, 151, 251, 351, 751, 851, and 951: Adhesion starting point
61, 661, and 1061: Rising edge
62, 562, and 662: Free end
C2: Colored notched section
D: Interspace

The invention claimed is:

1. An absorbent article comprising:
a liquid-permeable topsheet positioned at a surface that is contactable with a human body;
a non liquid-permeable backsheet positioned at a surface opposite to the topsheet;
an absorbent body provided between the topsheet and the backsheet; and
three-dimensional gathers formed at the topsheet side to be raised at both side portions in a longitudinal direction of the absorbent body;
wherein portions of the topsheet along both sides in the longitudinal direction of the absorbent body are folded up to the topsheet side and are adhered to the topsheet;
wherein the backsheet covers the absorbent body so as to cover from a bottom face of the absorbent body to side surfaces of the absorbent body, and the backsheet includes folding portions which are folded up to the topsheet side along both side portions in the longitudinal direction of the absorbent body;
wherein a part of each of the folding portions is adhered along a corresponding one of the folded portions of the topsheet, so as to cover both of the folded portions of the topsheet and so as to be flat along both side portions in the longitudinal direction of the absorbent body;
wherein non liquid-permeable nonwoven fabrics are adhered to surfaces that are opposite to surfaces of the folding portions that face the topsheet to form the three-dimensional gathers;
wherein the non liquid-permeable nonwoven fabrics are adhered to the flat folding portions so as to form flat root portions of the three-dimensional gathers along both side portions in the longitudinal direction of the absorbent body; and
wherein the three-dimensional gathers are raised from the flat root portions along both side portions in the longitudinal direction of the absorbent body.

2. The absorbent article according to claim 1, wherein the three-dimensional gathers comprise the folding portions and the non liquid-permeable nonwoven fabrics which are at least partially adhered to the folding portions, wherein the three-dimensional gathers have free ends structured with the non liquid-permeable nonwoven fabrics.

3. The absorbent article according to claim 2, wherein the non liquid-permeable nonwoven fabrics are adhered to the backsheet from adhesion starting points that are at an inner side in a width direction than folding starting points of the folding portions.

4. An inner absorbent article, comprising:
a liquid-permeable topsheet positioned at a surface that is contactable with a human body;
a non liquid-permeable backsheet positioned at a surface opposite to the topsheet;
an absorbent body provided between the topsheet and the backsheet; and
three-dimensional gathers formed at the topsheet side to be raised at both side portions in a longitudinal direction of the absorbent body;
wherein portions of the topsheet along both sides in the longitudinal direction of the absorbent body are folded up to the topsheet side and are adhered to the topsheet;
wherein the backsheet covers the absorbent body so as to cover from a bottom face of the absorbent body to side surfaces of the absorbent body, and the backsheet includes folding portions which are folded up to the topsheet side along both side portions in the longitudinal direction of the absorbent body;
wherein a part of each of the folding portions is adhered along a corresponding one of the folded portions of the topsheet, so as to cover both of the folded portions of the topsheet and so as to be flat along both side portions in the longitudinal direction of the absorbent body;
wherein non liquid-permeable nonwoven fabrics are adhered to surfaces that are opposite to surfaces of the folding portions that face the topsheet to form the three-dimensional gathers;
wherein the non liquid-permeable nonwoven fabrics are adhered to the flat folding portions so as to form flat root portions of the three-dimensional gathers along both side portions in the longitudinal direction of the absorbent body; and
wherein the three-dimensional gathers are raised from the flat root portions along both side portions in the longitudinal direction of the absorbent body.

* * * * *